(12) United States Patent
Wurdinger et al.

(10) Patent No.: US 10,174,365 B2
(45) Date of Patent: Jan. 8, 2019

(54) METHOD OF ANALYSING A BLOOD SAMPLE OF A SUBJECT FOR THE PRESENCE OF A DISEASE MARKER

(75) Inventors: Thomas Wurdinger, Amsterdam (NL); Rolf Jonas Nilsson, Amsterdam (NL)

(73) Assignees: STICHTING VU-VUMC, Amsterdam (NL); VERENIGING VOOR CHRISTELIJK HOGER ONDERWIJS, WETENSCHAPPELIJK ONDERZOEK EN PATIENTENZORG, Amsterdam (NL)

( * ) Notice: Subject to any disclaimer, the term of this patent is extended or adjusted under 35 U.S.C. 154(b) by 509 days.

(21) Appl. No.: 14/006,089

(22) PCT Filed: Jan. 16, 2012

(86) PCT No.: PCT/NL2012/050025
§ 371 (c)(1),
(2), (4) Date: Mar. 26, 2014

(87) PCT Pub. No.: WO2012/128616
PCT Pub. Date: Sep. 27, 2012

(65) Prior Publication Data
US 2014/0199693 A1    Jul. 17, 2014

(30) Foreign Application Priority Data

Mar. 18, 2011 (EP) .................... 11158912
May 27, 2011 (EP) .................... 11167973
Jul. 15, 2011 (WO) ............. PCT/NL2011/050518

(51) Int. Cl.
C12Q 1/68        (2018.01)
C12Q 1/6834     (2018.01)
C12Q 1/6886     (2018.01)

(52) U.S. Cl.
CPC ......... *C12Q 1/6834* (2013.01); *C12Q 1/6886* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 5,185,244 | A | 9/1993 | Wallace |
| 2003/0119003 | A1 | 6/2003 | Simons |
| 2004/0014059 | A1* | 1/2004 | Liew .................. C12Q 1/6809 435/6.16 |
| 2004/0137470 | A1 | 7/2004 | Dhallan |
| 2005/0069875 | A1 | 3/2005 | Schuh et al. |
| 2006/0288432 | A1 | 12/2006 | Vainchenker et al. |
| 2007/0059774 | A1 | 3/2007 | Grisham et al. |
| 2007/0059781 | A1 | 3/2007 | Kapur et al. |
| 2008/0038764 | A1 | 2/2008 | Yin |
| 2010/0184069 | A1 | 7/2010 | Fernando et al. |
| 2013/0196873 | A1 | 8/2013 | Wurdinger et al. |
| 2014/0256590 | A1 | 9/2014 | Wurdinger et al. |

FOREIGN PATENT DOCUMENTS

| CN | 103168235 A | 6/2013 |
| GB | 2380194 | 4/2003 |
| WO | WO 2000 63441 | 10/2000 |
| WO | WO 2002 070738 | 9/2002 |
| WO | 2005/043121 A2 | 5/2005 |
| WO | 2007/035585 A2 | 3/2007 |
| WO | 2008/156858 A2 | 12/2008 |
| WO | WO2010/139811 | * 12/2010 |
| WO | 2012008839 | 1/2012 |
| WO | 2012/128616 A1 | 9/2012 |
| WO | 2013/022342 A1 | 2/2013 |

OTHER PUBLICATIONS

Healy et al. Circulation. 2006;113:2278-2284.*
Claverley et al. (Clin Transl Sci 2010 3(5) 227-232).*
Girardot et al. (Blood, 2010, vol. 116, No. 3, pp. 437-445.*
Affymetrix Netaffx search results for PCA3 on human exon 1.0 ST array. Obtained from https://www.affymetrix.com/analysis/netaffx/showresults.affx on Jul. 17, 2017, 1 page.*
Affymetrix Netaffx search results for KLK3 on human exon 1.0 ST array. Obtained from https://www.affymetrix.com/analysis/netaffx/exon/transcript.affx?pk=1:3839538 on Jul. 17, 2017, 3 pages.*
Schutte M, Elstrodt F, Bralten LBC, Nagel JHA, Duijm E, et al. (2008) Exon Expression Arrays as a Tool to Identify New Cancer Genes. PLoS One 3(8): e3007. doi:10.1371/journal.pone.0003007 (Year: 2008).*
Affymetrix results, Details for Cluster 3002640, EGFR, obtained from https://www.affymetrix.com/analysis/netaffx/exon/transcript.affx?pk=1:3002640 on Jan. 3, 2018, 13 pages (Year: 2018).*
Calverley et al., "Significant Downregulation of Platelet Gene Expression in Metastatic Lung Cancer," Clinical Transl. Sci., 3(5): 227-232 (2010).
Skog et al., "Glioblastoma Microvesicles Transport RNA and Proteins that Promote Tumour Growth and Provide Diagnostic Biomarkers," Nature Cell Biology, 10(12):1470-1476 (2008).

(Continued)

Primary Examiner — Juliet C Switzer
(74) Attorney, Agent, or Firm — McDermott Will & Emery LLP

(57) ABSTRACT

The present invention relates to a method of analyzing a blood sample of a subject for the presence of a disease marker, said method comprising the steps of a) extracting nucleic acid from anucleated blood cells in said blood sample to provide an anucleated blood cells-extracted nucleic acid fraction, and b) analyzing said anucleated blood cells-extracted nucleic acid fraction for the presence of a disease marker, wherein said disease marker is a disease-specific mutation in a gene of a cell of said subject, or wherein said disease marker is a disease-specific expression profile of genes of a cell of said subject.

6 Claims, 8 Drawing Sheets
Specification includes a Sequence Listing.

(56) References Cited

OTHER PUBLICATIONS

Lood et al., "Platelet Transcriptional Profile and Protein Expression in Patients with Systemic Lupus Erythematosus: Up-Regulation of the Type I Interferon System is Strongly Associated with Vascular Disease,"116:1951-1957 (2010).
International Search Report from International Application No. PCT/NL2011/050518, dated Mar. 9, 2012.
International Search Report from International Application No. PCT/NL2012/050025, dated Jul. 2, 2012.
International Search Report from International Application No. PCT/NL2012/050550 dated Oct. 31, 2012.
Sidransky "Emerging Molecular Markers of Cancer," Nature Reviews Cancer 2(3): 210-219 (2002).
Giradot et al., "miR-28 is a Thrombopoietin Receptor Targeting MicroRNA Detected in a Fraction of Myeloproliferative Neoplasm Patient Platelets," Blood 116(3): 437-445 (2010).
Gnatenko et al., "Class Prediction Models of Thrombocytosis Using Genetic Biomarkers," Blood 115(1):7-14 (2010).
Al-Mufti et al., "Detection of Fetal Messenger Ribonucleic Acid in Maternal Blood to Determine Fetal RhD Status as a Strategy for Noninvasive Prenatal Diagnosis," Am. J. Obstet. Gynecol., 179:210-214 (1998).
Hahn et al., "Determination of Fetal Chromosome Aberrations from Fetal DNA in Maternal Blood: Has the Challenge Finally Been Met?," Expert Reviews in Molecular Medicine, 13:1-14 (2011).
Kolialexi et al., "Noninvasive Prenatal Diagnosis of beta-Thalassaemia Using Individual Fetal Erythroblasts Isolated from Maternal Blood After Enrichment," Prenatal Diagnosis, 27:1228-1232 (2007).
Lee et al., "Separation of Model Mixtures of Epsilon-Globin Positive Fetal Nucleated Red Blood Cells and Anucleate Erythrocytes Using a Microfluidic Device," Journal of Chromatography, 1217:1862-1866 (2010).
Nagalla et al., "Platelet RNA Chips Dip Into Thrombocytosis", Blood, 115:2-3 (2010).
Ramaswamy et al., "Multiclass Cancer Diagnosis Using Tumor Gene Expression Signatures", PNAS, 98(26): 15149-15154 (2001).
Su et al., "Molecular Classification of Human Carcinomas by Use of Gene Expression Signatures," Cancer Research, 61: 7388-7393 (2001).
Lu et al., "MicroRNA Expression Profiles Classify Human Cancers," Nature, 435:834-838 (2005).
Campbell, et al., Definition of subtypes of essential thrombocythaemia and relation to polycythaemia vera based on JAK2 V617 mutation status: a prostective study, The Lancet, Lancet Limited, Dec. 5, 2005, vol. 366, No. 9501, pp. 1945-1953, London, GB.
Ozeki, et al., A family having type 2B von Willebrand disease with an R1306W mutation: Severe thrombocytopenia leads to the normalization of high molecular weight multimers, Feb. 1, 2010, vol. 125, No. 2, Tarrytown, NY.
Raghavachari, et al., Amplified expression profiling of platelet transcriptome reveals changes in arginine metabolic pathways in patients with sickle cell disease, Circulation, Mar. 27, 2007, vol. 115, No. 12, pp. 1-22.
Salven, et al., Leukocytes and platelets of patients with cancer contain high levels of vascular endothelial growth factor, Clinical Cancer Research, The American Association for Cancer Research, Mar. 1, 1999, vol. 5, No. 3, US.
Nilsson, et al., "Blood platelets contain tumor-derived RNA biomarkers", Blood, American Society of Hematology, 2011, vol. 118, No. 13, pp. 3680-3683.
Go, et al., "C21ORF105, A chromosome 21-encoded mRNA, is not a discriminative marker gene for prediction of Down syndrome in maternal plasma", Prenatal Diagnosis, 2007, vol. 27, pp. 146-149.
Nong et al., "Nitric Oxide Inhalation Inhibits Platelet Aggregation and Platelet-Mediated Pulmonary Thrombosis in Rats", Circulation Research, 1997, 81:865-869.
Tuttle et al., "Placental Lactogen is Expressed but is not Translated into Protein in Breast Cancer", PLOS One, 2014, 9(1): e87325.
Ng et al., "mRNA of Placental origin is Readily Detectable in Maternal Plasma", PNAS, 2003, 100:4748-4753.
Yanabu et al., "Tyrosine Phosphorylation and p72syk Activation by an Anti-glycoprotein Ib Monoclonal Antibody", Blood, 1997, 89(5): 1590-1598.
Alevizos, I., et al., "MicroRNAs in Sjogren's Syndrome as a Prototypic Autoimmune Disease," Autoimmun Rev., Jul. 2010, v. 9, pp. 681-621.
Hill, A., "Exosomes in Neurological Disease," Neurology (2009), v. 25, pp. 27-32.
Free Dictionary Definition for 'Device'. Available via url:<thefreedictionary.com/device>, printed on Jul. 31, 2017.
Dittrich et al., "Analysis of SAGE data in human platelets: Features of the transcriptome in an anucleate cell". Throm Haemost 95 (4): 643-651, 2006.
Croix et al., MicroSAGE Manual version 1.0e, obtained from www.sagenet.org/protocol/ year: 2000.
Ji et al., "Epidermal growth factor receptor variant III mutations in lung tumorigenesis and sensitivity to tyrosine kinase inhibitors", PNAS, 2006, 103, 7817-7822.
Zschocke et al., "A fluorescent multiplex ARMS method for rapid mutation analysis", Molecular and Cellular Probes, 1995, 9, 447-451.
Yoshimoto et al., "Development of a real-time RT-PCR assay for detecting EGFRvIII in glioblastoma samples", Clin Cancer Res 2008, 14 (2):488-493.

\* cited by examiner

A

Microvesicle preparation from serum sample

B

Microvesicle preparation from plasma sample

| ProbeName | GeneName | SEQ ID NO |
|---|---|---|
| A_23_P106617 | WFDC1 | SEQ ID NO:13 |
| A_23_P68851 | KREMEN1 | SEQ ID NO:14 |
| A_23_P111206 | FKBP5 | SEQ ID NO:15 |
| A_23_P259292 | C1QTNF5 | SEQ ID NO:16 |
| A_23_P5392 | TP53I3 | SEQ ID NO:17 |
| A_24_P55092 | CD109 | SEQ ID NO:18 |
| A_23_P111321 | ARG1 | SEQ ID NO:19 |
| A_23_P175881 | THC2325987 | SEQ ID NO:20 |
| A_23_P38154 | FDXR | SEQ ID NO:21 |
| A_32_P167111 | A_32_P167111 | SEQ ID NO:22 |
| A_23_P17811 | SEC14L2 | SEQ ID NO:23 |
| A_32_P132718 | BC018626 | SEQ ID NO:24 |
| A_32_P176018 | ACTL8 | SEQ ID NO:25 |
| A_23_P201587 | SORT1 | SEQ ID NO:26 |
| A_23_P85008 | MAOB | SEQ ID NO:27 |
| A_23_P171237 | ACRC | SEQ ID NO:28 |
| A_23_P122863 | GRB10 | SEQ ID NO:29 |
| A_23_P326080 | DEFA1 | SEQ ID NO:30 |
| A_23_P330561 | MCEMP1 | SEQ ID NO:31 |
| A_23_P171336 | NXF3 | SEQ ID NO:32 |
| A_23_P75398 | IL1R2 | SEQ ID NO:33 |
| A_23_P142183 | ENST00000285206 | SEQ ID NO:34 |
| A_23_P151415 | KATNAL1 | SEQ ID NO:35 |
| A_23_P218086 | TPCN1 | SEQ ID NO:36 |
| A_23_P253791 | CAMP | SEQ ID NO:37 |
| A_23_P31816 | DEFA3 | SEQ ID NO:38 |
| A_23_P58266 | S100P | SEQ ID NO:39 |
| A_23_P166818 | LTF | SEQ ID NO:40 |
| A_24_P270033 | ENST00000278949 | SEQ ID NO:41 |
| A_23_P126135 | MPN2 | SEQ ID NO:42 |

METHOD OF ANALYSING A BLOOD SAMPLE OF A SUBJECT FOR THE PRESENCE OF A DISEASE MARKER

RELATED APPLICATIONS

This application is the U.S. National Stage of International Application No. PCT/NL2012/050025, filed Jan. 16, 2012, published in English, and claims the benefit of European Application No. 11158912.3, filed on Mar. 18, 2011, European Application No. 11167973.4, filed on May 27, 2011, and International Application No. PCT/NL2011/050518, filed on Jul. 15, 2011, the entire teachings of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 25, 2013, is named P91312US10 sequence list_ST25.txt and is 8 KB in size.

FIELD OF THE INVENTION

The invention is in the field of medical diagnostics, in particular in the field of disease diagnostics and monitoring. The invention is directed to markers for the detection of disease, to methods for detecting disease, and to a method for determining the efficacy of a disease treatment.

BACKGROUND OF THE INVENTION

In clinical practice there is a strong need to be able to detect disease in its earliest stages, to predict disease progression, and to implement patient-tailored therapy. Early detection of in particular neoplastic disease (cancer) is critical to ensure favourable treatment of the disease. In spite of numerous advances in medical research, cancer remains a major cause of death worldwide. When patients seek treatment, they are generally exhibiting symptoms of distant metastases, meaning that too often the cancer is detected too late.

Lung, prostate, breast, and colon cancer are the most common tumours, and in order to facilitate appropriate remedial action by surgical resection, radiotherapy, chemotherapy, or other known treatment methods there is a need for rapid and simple methods for the early diagnoses of cancer. The availability of good diagnostic methods for cancer is also important to assess patient responses to treatment, or to assess recurrence due to re-growth at the original site or metastasis.

Several types of cancer markers, such as, for example, oncogene products, growth factors and growth factor receptors, angiogenic factors, proteases, adhesion factors and tumour suppressor gene products, etc, are presently known and are not only considered essential for early diagnosis, but also for differential diagnosis of patients with uncertain clinical abnormalities such as for distinguishing malignant from benign abnormalities; for predicting the likelihood of response in a particular patient with established malignancy to a selected therapeutic method of treatment; and for providing information concerning the risk, presence, status, or future behaviour of the malignancy in a human or animal subject. Currently, the ability to detect and diagnose cancer through the detection of tumour or cancer markers is an area of widespread interest and as a consequence the need exists for reproducible and reliable methods of identifying new and more useful cancer markers in patient specimens.

Glioblastoma is the most common and most aggressive type of primary brain tumor in humans. The disease is difficult to diagnose and even harder to treat due, in part, to the blood-brain barrier that hinders the delivery of therapeutic agents and detection of potentially important diagnostic markers. Diagnostic markers for glioblastoma are available, but are specific for the tumour tissue itself and require a tumour sample.

Improved screening and detection methods are needed in order to detect cancer in an early phase and to follow the progression of the disease. In the case of cancer we are at a state where we do not only need to detect the tumour, but also need to detect it before it has reached a point of no return, where the treatment becomes palliative instead of curative. People at risk, as well as patients with recurring cancer, should be monitored extensively. Furthermore, since tumours can respond differently to different therapeutics, patient stratification is becoming of importance.

Genetic analysis using tumour biopsies has allowed the identification of many mutations that are useful for diagnosis of the cancer as well as for emerging patient stratification strategies. However, a disadvantage of current genetic analysis of tumours is the need for tumour biopsies, which are often impossible to dissect from patients. Furthermore, the use of biopsies is static and does not allow genetic monitoring of tumour progression or recurrence over time. Moreover, many tumours are heterogeneous, resulting in potential false-positive or false-negative genetic characterization of biopsies of such tumours.

Recently, the use of circulating tumour cells for diagnosis and monitoring of tumour progression or recurrence showed the use of blood as a source of tumour-derived material, notably tissue fragments in the form of cells. However, the use of circulating tumour cells is inefficient for most cancers.

Calverley et al (Clinical and Translational Science vol 3, issue 5, 2010) disclose a down-regulation of gene expression of platelets in metastatic lung cancer. The authors identified 200 genes that appeared to be differentially expressed between healthy persons and patients. According to the authors, the platelet proteome is mirrored in the transcriptome of the platelet. The gene expression as measured was correlated to genes from megakaryocytes. No disclosure is made that RNA/DNA derived from other cells than megakaryocytes was measured when testing the thrombocytes, and no indication that circulating RNA/DNA derived from other cells can be taken up by thrombocytes.

In general, a disease marker is defined as a compound of which the concentration is altered, preferably elevated, in a biological fluid from a diseased patient when compared to a normal healthy subject, and which may subsequently be used as a marker compound indicative of a disease. Yet, the identification of specific compounds, for instance proteins, in various body fluids as markers of disease, such as cancer, has been hampered by the lack of suitable techniques therefore.

Also in case of diseases other than cancer, markers may be available that are difficult to detect. This hampers early diagnosis of the disease.

Lood et al (Blood vol 116, no 11, 2010) disclose that the gene expression of IFN-I regulated genes in platelets in patients with SLE is increased. The authors hypothesize that IFNalpha influences gene expression in megakaryocytes, resulting in an increased level of IFN-I regulated proteins in platelets. The expressions of genes from megakaryocytes are thus correlated to SLE or vascular disease. No disclosure is made that RNA/DNA from diseased cells may be taken up by platelets.

The present invention aims to overcome the problem of the prior art that not all diseased tissues or disease types (e.g. tumours) result in circulating disease cells (e.g. circulating tumour cells). The present invention also aims to overcome the problem that protein markers for detecting diseases such as cancer are difficult to detect. Further, the present invention aims to provide methods that do not require biopsies, and allow extensive monitoring of patients.

SUMMARY OF THE INVENTION

The present invention in a first aspect provides a method of analysing a blood sample of a subject for the presence of a disease marker, said method comprising the steps of a) extracting nucleic acid from anucleated blood cells, preferably thrombocytes, in said blood sample to provide an anucleated blood cell-extracted nucleic acid fraction, and b) analysing said anucleated blood cell-extracted nucleic acid fraction for the presence of a disease marker, wherein said disease marker is a disease-specific mutation in a gene of a nucleated cell of said subject, or wherein said disease marker is a disease-specific expression profile of genes of a nucleated cell of said subject.

It was surprisingly found that nucleic acids from nucleated cells are present in anucleated blood cells such as thrombocytes. It may be that nucleated cells excrete nucleic acids into the blood stream and these excreted nucleic acids are then taken up from the blood stream by anucleated cells such as thrombocytes or that in some other way of transport nucleic acids from nucleated cells are transferred to anucleated blood cells. The inventors realized for the first time that disease markers may be used on the nucleic acids extracted from anucleated blood cells to identify diseases from nucleated cells.

In a preferred embodiment of the method of the invention said anucleated blood cell-extracted nucleic acid fraction comprises nucleic acid originating from a nucleated cell. In a preferred embodiment of the present invention and embodiments thereof, the anucleated blood cell-extracted nucleic acid fraction is not megakaryocyte-derived nucleic acid or megakaryocyte-derived RNA, i.e. the nucleic acid fraction to be tested is not of megakaryocyte-lineage or megakaryocyte genomic origin.

The term "anucleated blood cell" as used herein refers to a cell that lacks a nucleus. The term includes reference to both erythrocyte and thrombocyte. Preferred embodiments of anucleated cells in aspects of this invention are thrombocytes. The term "anucleated blood cell" preferably does not include reference to cells that lack a nucleus as a result of faulty cell division.

The term "nucleated cell" as used herein refers to a cell having a nucleus. The term includes reference to somatic cells, germ cells and stem cells, and may include cells from colon, pancreas, brain, bladder, breast, prostate, lung, breast, ovary, uterus, liver, kidney, spleen, thymus, thyroid, nerve tissue, connective tissue, blood, epithelial tissue, lymph node, bone, muscle and skin tissues. The nucleated cell is preferably a cell from a diseased tissue. In a preferred embodiment, the nucleated cell is not a megakaryocyte.

Thus, the present invention is generally aimed at analysing nucleic acids that have been transferred from cells that have a nucleus into cells that have no nucleus, wherein the cells that have no nucleus can be easily isolated from the blood stream and contain nucleic acid from the nucleated cells. The term "nucleus" refers to the membrane-enclosed organelle found in eukaryotic cells that contains most of the cell's genetic material organized in the form of chromosomes. The genes within these chromosomes are the cell's nuclear genome. The interior of the nucleus contains a number of subnuclear bodies including the RNA-comprising nucleolus, which is mainly involved in the assembly of RNA-comprising ribosomes. After being produced in the nucleolus, ribosomes are exported to the cytoplasm where they translate mRNA.

An anucleated blood cell-extracted nucleic acid fraction preferably refers to a fraction comprising chromosomal DNA, ribosomal RNA, nucleolus RNA, and/or messenger RNA.

The term "gene" as used herein, and in particular in the phrasing "mutation in a gene of a nucleated cell" is meant to refer to any nucleic acid sequence, both chromosomal and extra-chromosomal, of a nucleated (somatic) cell, preferably a nuclear nucleic acid sequence, and may include transcribed and non-transcribed sequences as well as ribosomal RNA sequences, most preferably chromosomal sequences that are transcribed into RNA.

In a preferred embodiment of a method of the invention said disease-specific mutation is in a chromosomal gene.

In another preferred embodiment, said gene is not a gene from an anucleated blood cell. In another preferred embodiment, said gene is not a gene from a megakaryocyte. In yet another preferred embodiment said gene is not CD109.

In a preferred embodiment of a method of the invention said disease-specific expression profile is the expression profile of chromosomal genes. In particular of chromosomal genes from a nucleated cell the mRNA of which is present in a thrombocyte.

In another preferred embodiment of a method of the invention said nucleic acid is ribonucleic acid (RNA), more preferably messenger ribonucleic acid (mRNA).

In a preferred embodiment of a method of the invention said nucleic acid is not mtDNA. Hence, mitochondrial nucleic acid is preferably not an aspect of the present invention.

In another preferred embodiment of a method of analysing a blood sample according to the invention said step b) of analysing said anucleated blood cell-extracted nucleic acid fraction for the presence of a disease marker comprises the selective amplification of:
i) said mutation by reverse transcriptase polymerase chain reaction amplification using at least one nucleic acid mutation-specific amplification primer or probe, or
ii) a plurality of mRNAs by reverse transcriptase polymerase chain reaction amplification to determine the expression level of the chromosomal genes encoding said mRNAs to thereby provide an expression profile for said genes and comparing said expression profile to a reference profile.

The blood sample is preferably outside the body.

In a preferred embodiment of a method of the invention the disease is selected from the group consisting of cancer, autoimmune disease, skin diseases, eye disease, endocrine diseases, neurological disorders, and cardiovascular diseases.

In another preferred embodiment of a method of the invention said disease is selected from the group consisting of autoimmune disease, skin diseases, eye disease, endocrine diseases, neurological disorders, and cardiovascular diseases.

In another preferred embodiment of a method of the invention said disease is cancer.

In yet another preferred embodiment of a method of the invention said cancer is a solid tumour cancer, preferably selected from colon, pancreas, brain, bladder, breast, prostate, lung, breast, ovary, uterus, liver, kidney, spleen, thymus, thyroid, nerve tissue, epithelial tissue, lymph node, bone, muscle and skin.

In another preferred embodiment of a method of the invention said disease is not cancer.

In another preferred embodiment of a method of the invention said disease is not a vascular disease.

In another preferred embodiment of a method of the invention said disease is not systemic lupus erythematosus.

In another preferred embodiment of a method of the invention said disease is not sickle cell disease.

In another preferred embodiment of a method of the invention said disease is not Alzheimer's disease.

In another preferred embodiment of a method of the invention said disease is not a disease associated with pathological megakaryocyte function.

In another preferred embodiment of a method of the invention said disease is not a disease associated with pathological platelet function.

The above embodiments that are disclaimed in preferred embodiments may be combined in any combination.

In another preferred embodiment of a method of the invention said disease is selected from the group consisting of autoimmune disease, skin diseases, eye disease, endocrine diseases, and neurological disorders.

In preferred embodiments of aspects of the invention the auto-immune disease is selected from the group consisting of Achlorhydra Autoimmune Active Chronic Hepatitis; Acute Disseminated Encephalomyelitis; Acute hemorrhagic leukoencephalitis; Addison's Disease; Agammaglobulinemia; Alopecia greata; Amyotrophic Lateral Sclerosis; Ankylosing Spondylitis; Anti-GBM/TBM Nephritis; Antiphospholipid syndrome; Antisynthetase syndrome; polyarticular Arthritis; Atopic allergy; Atopic Dermatitis; Autoimmune Aplastic Anemia; Autoimmune cardiomyopathy; Autoimmune enteropathy; Autoimmune hemolytic anemia; Autoimmune hepatitis; Autoimmune inner ear disease; Autoimmune lymphoproliferative syndrome; Autoimmune peripheral neuropathy; Autoimmune pancreatitis; Autoimmune polyendocrine syndrome; Autoimmune progesterone dermatitis; Autoimmune thrombocytopenic purpura; Autoimmune uveitis; Balo disease/Balo concentric sclerosis; Bechets Syndrome; Berger's disease; Bickerstaffs encephalitis; Blau syndrome; Bullous Pemphigoid; Castleman's disease; Celiac disease; Chagas disease; Chronic Fatigue Immune Dysfunction Syndrome; Chronic inflammatory demyelinating polyneuropathy; Chronic recurrent multifocal osteomyelitis; Chronic lyme disease; Chronic obstructive pulmonary disease; Churg-Strauss syndrome; Cicatricial Pemphigoid; Coeliac Disease; Cogan syndrome; Cold agglutinin disease; Complement component 2 deficiency; Cranial arteritis; CREST syndrome; Crohns Disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Dressler's syndrome; Discoid lupus erythematosus; Eczema; Endometriosis; Enthesitis-related arthritis; Eosinophilic fasciitis; Eosinophilic gastroenteritis; Epidermolysis bullosa acquisita; Erythema nodosum; Essential mixed cryoglobulinemia; Evan's syndrome; Fibrodysplasia ossificans progressiva; Fibromyalgia/Fibromyositis; Fibrosing aveolitis; Gastritis; Gastrointestinal pemphigoid; Giant cell arteritis; Glomerulonephritis; Goodpasture's syndrome; Graves' disease; Guillain-Barre syndrome; Hashimoto's encephalitis; Hashimoto's thyroiditis; Haemolytic anaemia; Henoch-Schonlein purpura; Herpes gestationis; Hidradenitis suppurativa; Hughes syndrome; Hypogammaglobulinemia; Idiopathic Inflammatory Demyelinating Diseases; Idiopathic pulmonary fibrosis; Idiopathic thrombocytopenic purpura; IgA nephropathy; Inclusion body myositis; Inflammatory demyelinating polyneuopathy; Interstitial cystitis; Irritable Bowel Syndrome (IBS); Juvenile idiopathic arthritis; Juvenile rheumatoid arthritis; Kawasaki's Disease; Lambert-Eaton myasthenic syndrome; Leukocytoclastic vasculitis; Lichen planus; Lichen sclerosus; Linear IgA disease; Lou Gehrig's Disease; Lupoid hepatitis; Lupus erythematosus; Majeed syndrome; Ménière's disease; Microscopic polyangiitis; Miller-Fisher syndrome; Mixed Connective Tissue Disease; Morphea; Mucha-Habermann disease; Muckle-Wells syndrome; Multiple Myeloma; Multiple Sclerosis; Myasthenia gravis; Myositis; Narcolepsy; Neuromyelitis optica; Neuromyotonia; Occular cicatricial pemphigoid; Opsoclonus myoclonus syndrome; Ord thyroiditis; Palindromic rheumatism; PANDAS; Paraneoplastic cerebellar degeneration; Paroxysmal nocturnal hemoglobinuria; Parry Romberg syndrome; Parsonnage-Turner syndrome; Pars planitis; Pemphigus; Pemphigus vulgaris; Pernicious anaemia; Perivenous encephalomyelitis; POEMS syndrome; Polyarteritis nodosa; Polymyalgia rheumatica; Polymyositis; Primary biliary cirrhosis; Primary sclerosing cholangitis; Progressive inflammatory neuropathy; Psoriasis; Psoriatic Arthritis; Pyoderma gangrenosum; Pure red cell aplasia; Rasmussen's encephalitis; Raynaud phenomenon; Relapsing polychondritis; Reiter's syndrome; Restless leg syndrome; Retroperitoneal fibrosis; Rheumatoid arthritis; Rheumatoid fever; Sarcoidosis; Schizophrenia; Schmidt syndrome; Schnitzler syndrome; Scleritis; Scleroderma; Sjögren's syndrome; Spondyloarthropathy; Sticky blood syndrome; Still's Disease; Stiff person syndrome; Subacute bacterial endocarditis (SBE); Susac's syndrome; Sweet syndrome; Sydenham Chorea; Sympathetic ophthalmia; Takayasu's arteritis; Temporal arteritis; Tolosa-Hunt syndrome; Transverse Myelitis; Ulcerative Colitis; Undifferentiated connective tissue disease; Undifferentiated spondyloarthropathy; Vasculitis; Vitiligo; Wegener's granulomatosis; Wilson's syndrome; and Wiskott-Aldrich syndrome.

In other preferred embodiments of aspects of the invention the skin disease is selected from the group consisting of Acneiform eruptions; Autoinflammatory syndromes; Chronic blistering; Conditions of the mucous membranes; Conditions of the skin appendages; Conditions of the subcutaneous fat; Congenital anomalies; Connective tissue diseases (such as Abnormalities of dermal fibrous and elastic tissue); Dermal and subcutaneous growths; Dermatitis (including Atopic Dermatitis, Contact Dermatitis, Eczema, Pustular Dermatitis, and Seborrheic Dermatitis); Disturbances of pigmentation; Drug eruptions; Endocrine-related skin disease; Eosinophilic; Epidermal nevi, neoplasms, cysts; Erythemas; Genodermatoses; Infection-related skin disease; Lichenoid eruptions; Lymphoid-related skin disease; Melanocytic nevi and neoplasms (including Melanoma); Monocyte- and macrophage-related skin disease; Mucinoses; Neurocutaneous; Noninfectious immunodeficiency-related skin disease; Nutrition-related skin disease; Papulosquamous hyperkeratotic (including Palmoplantar keratodermas); Pregnancy-related skin disease; Pruritic; Psoriasis; Reactive neutrophilic; Recalcitrant palmoplantar eruptions; Resulting from errors in metabolism; Resulting from physical factors (including Ionizing radiation-induced); Urticaria and angioedema; Vascular-related skin disease.

In other preferred embodiments of aspects of the invention the endocrine disease is selected from the group consisting of Adrenal disorders; Glucose homeostasis disorders; Thyroid disorders; Calcium homeostasis disorders and Metabolic bone disease; Pituitary gland disorders; and Sex hormone disorders.

In other preferred embodiments of aspects of the invention the eye disease is selected from the group consisting of H00-H06 Disorders of eyelid, lacrimal system and orbit; H10-H13 Disorders of conjunctiva; H15-H22 Disorders of sclera, cornea, iris and ciliary body; H25-H28 Disorders of lens; H30-H36 Disorders of choroid and retina (including H30 Chorioretinal inflammation, H31 Other disorders of choroid, $H_{32}$Chorioretinal disorders in diseases classified elsewhere, H33 Retinal detachments and breaks, H34 Retinal vascular occlusions, H35 Other retinal disorders, and H36 Retinal disorders in diseases classified elsewhere); H40-H42 Glaucoma; H43-H45 Disorders of vitreous body and globe; H46-H48 Disorders of optic nerve and visual pathways; H49-H52 Disorders of ocular muscles, binocular movement, accommodation and refraction; H53-H54.9 Visual disturbances and blindness; and H55-H59 Other disorders of eye and adnexa.

In other preferred embodiments of aspects of the invention the neurological disorder is selected from the group consisting of Abarognosis; Acquired Epileptiform Aphasia; Acute disseminated encephalomyelitis; Adrenoleukodystrophy; Agenesis of the corpus callosum; Agnosia; Aicardi syndrome; Alexander disease; Alien hand syndrome; Allochiria; Alpers' disease; Alternating hemiplegia; Alzheimer's disease; Amyotrophic lateral sclerosis (see Motor Neurone Disease); Anencephaly; Angelman syndrome; Angiomatosis; Anoxia; Aphasia; Apraxia; Arachnoid cysts; Arachnoiditis; Arnold-Chiari malformation; Arteriovenous malformation; Ataxia Telangiectasia; Attention deficit hyperactivity disorder; Auditory processing disorder; Autonomic Dysfunction; Back Pain; Batten disease; Behcet's disease; Bell's palsy; Benign Essential Blepharospasm; Benign Intracranial Hypertension; Bilateral frontoparietal polymicrogyria; Binswanger's disease; Blepharospasm; Bloch-Sulzberger syndrome; Brachial plexus injury; Brain abscess; Brain damage; Brain injury; Brain tumor; Brown-Séquard syndrome; Canavan disease; Carpal tunnel syndrome; Causalgia; Central pain syndrome; Central pontine myelinolysis; Centronuclear myopathy; Cephalic disorder; Cerebral aneurysm; Cerebral arteriosclerosis; Cerebral atrophy; Cerebral gigantism; Cerebral palsy; Cerebral vasculitis; Cervical spinal stenosis; Charcot-Marie-Tooth disease; Chiari malformation; Chorea; Chronic fatigue syndrome; Chronic inflammatory demyelinating polyneuropathy (CIDP); Chronic pain; Coffin Lowry syndrome; Coma; Complex regional pain syndrome; Compression neuropathy; Congenital facial diplegia; Corticobasal degeneration; Cranial arteritis; Craniosynostosis; Creutzfeldt-Jakob disease; Cumulative trauma disorders; Cushing's syndrome; Cytomegalic inclusion body disease (CIBD); Cytomegalovirus Infection; Dandy-Walker syndrome; Dawson disease; De Morsier's syndrome; Dejerine-Klumpke palsy; Dejerine-Sottas disease; Delayed sleep phase syndrome; Dementia; Dermatomyositis; Developmental dyspraxia; Diabetic neuropathy; Diffuse sclerosis; Dravet syndrome; Dysautonomia; Dyscalculia; Dysgraphia; Dyslexia; Dystonia; Empty sella syndrome; Encephalitis; Encephalocele; Encephalotrigeminal angiomatosis; Encopresis; Epilepsy; Erb's palsy; Erythromelalgia; Essential tremor; Fabry's disease; Fahr's syndrome; Fainting; Familial spastic paralysis; Febrile seizures; Fisher syndrome; Friedreich's ataxia; Fibromyalgia; Gaucher's disease; Gerstmann's syndrome; Giant cell arteritis; Giant cell inclusion disease; Globoid Cell Leukodystrophy; Gray matter heterotopia; Guillain-Barré syndrome; HTLV-1 associated myelopathy; Hallervorden-Spatz disease; Head injury; Headache; Hemifacial Spasm; Hereditary Spastic Paraplegia; Heredopathia atactica polyneuritiformis; Herpes zoster oticus; Herpes zoster; Hirayama syndrome; Holoprosencephaly; Huntington's disease; Hydranencephaly; Hydrocephalus; Hypercortisolism; Hypoxia; Immune-Mediated encephalomyelitis; Inclusion body myositis; Incontinentia pigmenti; Infantile phytanic acid storage disease; Infantile Refsum disease; Infantile spasms; Inflammatory myopathy; Intracranial cyst; Intracranial hypertension; Joubert syndrome; Karak syndrome; Kearns-Sayre syndrome; Kennedy disease; Kinsbourne syndrome; Klippel Feil syndrome; Krabbe disease; Kugelberg-Welander disease; Kuru; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Lewy body dementia; Lissencephaly; Locked-In syndrome; Lou Gehrig's disease (See Motor Neurone Disease); Lumbar disc disease; Lumbar spinal stenosis; Lyme disease-Neurological Sequelae; Machado-Joseph disease (Spinocerebellar ataxia type 3); Macrencephaly; Macropsia; Megalencephaly; Melkersson-Rosenthal syndrome; Menieres disease; Meningitis; Menkes disease; Metachromatic leukodystrophy; Microcephaly; Micropsia; Migraine; Miller Fisher syndrome; Mini-stroke (transient ischemic attack); Mitochondrial myopathy; Mobius syndrome; Monomelic amyotrophy; Motor Neurone Disease; Motor skills disorder; Moyamoya disease; Mucopolysaccharidoses; Multi-infarct dementia; Multifocal motor neuropathy; Multiple sclerosis; Multiple system atrophy; Muscular dystrophy; Myalgic encephalomyelitis; Myasthenia gravis; Myelinoclastic diffuse sclerosis; Myoclonic Encephalopathy of infants; Myoclonus; Myopathy; Myotubular myopathy; Myotonia congenita; Narcolepsy; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Niemann-Pick disease; Non 24-hour sleep-wake syndrome; Nonverbal learning disorder; O'Sullivan-McLeod syndrome; Occipital Neuralgia; Occult Spinal Dysraphism Sequence; Ohtahara syndrome; Olivopontocerebellar atrophy; Opsoclonus myoclonus syndrome; Optic neuritis; Orthostatic Hypotension; Overuse syndrome; Palinopsia; Paresthesia; Parkinson's disease; Paramyotonia Congenita; Paraneoplastic diseases; Paroxysmal attacks; Parry-Romberg syndrome; Pelizaeus-Merzbacher disease; Periodic Paralyses; Peripheral neuropathy; Persistent Vegetative State; Pervasive developmental disorders; Photic sneeze reflex; Phytanic acid storage disease; Pick's disease; Pinched nerve; Pituitary tumors; PMG; Polio; Polymicrogyria; Polymyositis; Porencephaly; Post-Polio syndrome; Postherpetic Neuralgia (PHN); Postinfectious Encephalomyelitis; Postural Hypotension; Prader-Willi syndrome; Primary Lateral Sclerosis; Prion diseases; Progressive hemifacial atrophy; Progressive multifocal leukoencephalopathy; Progressive Supranuclear Palsy; Pseudotumor cerebri; Rabies; Ramsay-Hunt syndrome (Type I and Type II); Rasmussen's encephalitis; Reflex neurovascular dystrophy; Refsum disease; Repetitive motion disorders; Repetitive stress injury; Restless legs syndrome; Retrovirus-associated myelopathy; Rett syndrome; Reye's syndrome; Rhythmic Movement Disorder; Romberg syndrome; Saint Vitus dance; Sandhoff disease; Schizophrenia; Schilder's disease; Schizencephaly; Sensory integration dysfunction; Septo-optic dysplasia; Shaken baby syndrome; Shingles; Shy-Drager syndrome; Sjögren's syndrome; Sleep apnea; Sleeping sickness; Snatiation; Sotos syndrome; Spasticity; Spina bifida; Spinal cord injury; Spinal cord tumors; Spinal muscular atrophy; Spinocerebellar ataxia; Steele-Richardson-Olszewski syndrome; Stiff-person syndrome; Stroke; Sturge-Weber syndrome; Subacute sclerosing panencephalitis; Subcortical arteriosclerotic encephalopathy; Superficial siderosis; Sydenham's chorea; Syncope; Synesthesia; Syringomyelia; Tarsal tunnel syndrome; Tardive dyskinesia; Tarlov cyst; Tay-Sachs disease; Temporal arteritis; Tetanus; Tethered spinal cord syndrome; Thomsen disease; Thoracic outlet syndrome; Tic Douloureux; Todd's paralysis; Tourette syndrome; Toxic encephalopathy; Transient ischemic attack; Transmissible spongiform encephalopathies; Transverse myelitis; Traumatic brain injury; Tremor; Trigeminal neuralgia; Tropical spastic paraparesis; Trypanosomiasis; Tuberous sclerosis; Von Hippel-Lindau disease; Viliuisk Encephalomyelitis; Wallenberg's syndrome; Werdnig-Hoffman disease; West syndrome; Whiplash; Williams syndrome; Wilson's disease; and Zellweger syndrome.

In other preferred embodiments of aspects of the invention the cardiovascular disease is selected from the group consisting of Aneurysm; Angina; Atherosclerosis; Cerebrovascular Accident (Stroke); Cerebrovascular disease; Congestive Heart Failure; Coronary Artery Disease; Myocardial infarction (Heart Attack); and Peripheral vascular disease.

In other preferred embodiments of aspects of the invention the cardiovascular disease is not systemic lupus erythematosus.

In another aspect, the present invention provides a method of diagnosing disease in a subject using the method of analysing a blood sample according to the invention. Hence, in another preferred embodiment of a method of the invention, said method of analysing a blood sample according to the invention is part of a method of diagnosing disease in a subject, and wherein the presence of said disease marker in said anucleated blood cell-extracted nucleic acid fraction is indicative of said subject suffering from said disease.

In another aspect, the present invention provides a method for determining the efficacy of a disease treatment in a subject, comprising the steps of:
analysing a blood sample of a subject for the presence of a disease marker using the method of analysing a blood sample according to the invention at a first time point to thereby provide a first value for the level of said disease marker in said subject;
analysing a blood sample of said subject for the presence of a disease marker using the method of analysing a blood sample according to the invention at a second time point that is earlier or later, preferably later, than said first time point, to thereby provide a second value for the level of said disease marker in said subject, wherein said subject has been subjected to a disease treatment between said first and second time point, and
comparing said first and second value to determine the efficacy of said disease treatment in said subject.

The skilled artisan will understand that treatment prior to the first time point and subsequent measurements at a second, later, time point without any disease treatment having occurred between said time points, is included in aspects of the invention for determining the efficacy of a disease treatment.

In another aspect, the present invention provides a method for determining the stage of disease. In order to determine the stage of disease, it is beneficial to correlate disease marker values as determined by methods of this invention to disease stages. A single measurement of the disease marker may than be compared to one or more reference values to obtain an indication of the stage of the disease.

In another aspect, the present invention provides a method for determining the stage of disease in a subject, comprising the steps of:
analysing a blood sample of a subject for the presence of a disease marker using the method of analysing a blood sample of a subject for the presence of a disease marker according to the present invention to thereby provide a test value for the level of said disease marker in said subject,
providing a reference value for the level of said disease marker wherein said reference value is correlated to a particular stage of disease, and
comparing said test and reference value to determine the stage of disease in said subject.

In yet another aspect, the present invention provides a kit of parts adapted for performing a method of the invention as described herein above, the kit comprising a packaging material which comprises at least one of:
a container for holding anucleated blood cells, preferably thrombocytes, separated from a blood sample;
an agent for extracting nucleic acids from said anucleated blood cells;
an agent for selectively amplifying from said nucleic acids extracted from said anucleated blood cells a disease-specific marker as described herein above, such as a disease-specific mutation in a gene of a nucleated cell of a subject or a disease-specific expression profile of nucleic acid from a nucleated cell of said subject, for instance by reverse transcriptase polymerase chain reaction amplification, and
a printed or electronic instruction for performing a method of the invention as described herein above,
the kit further comprising:
a reference for said disease marker, wherein said reference is indicative for the presence or absence of said disease marker in said anucleated blood cells-extracted nucleic acid fraction.

In a preferred embodiment of a kit according to the present invention said reference is a reference value for the level of nucleic acids comprising said disease-specific mutation in anucleated blood cells in a healthy control subject or in a control subject suffering from disease, or wherein said reference is a reference expression profile, for instance for a plurality of mRNAs in anucleated blood cells from a healthy control subject or from a control subject suffering from disease.

In another preferred embodiment of a kit according to the present invention said agent or instruction is selected from a particle or fluorescent marker-labeled anti-anucleated blood cell antibody (preferably a fluorescent marker-labeled anti-thrombocyte antibody), an instruction for bead-based anucleated blood cells isolation (preferably thrombocyte isolation), an instruction for FACS sorting of anucleated blood cells (preferably of thrombocytes), an instruction for anucleated blood cell (preferably thrombocyte) recovery by centrifugation, or negative selection of non-anucleated blood cell components (preferably non-thrombocyte components).

In yet another aspect, the present invention provides a device for diagnosing disease, the device comprising a support and at least one agent for specifically determining a level and/or activity of at least one nucleic acid mutant in a anucleated blood cells sample of the subject, said agent being attached to said support, and a computer-readable medium having computer-executable instructions for performing a method of the invention as described herein above.

In a preferred embodiment of a device according to the present invention, said at least one agent is an oligonucleotide probe or sequencing primer.

In a preferred embodiment of a device according to the present invention, the device comprises a lateral flow device, a dipstick or a cartridge for performing a nucleic acid hybridization reaction between an anucleated blood cells-extracted nucleic acid and at least one nucleic acid mutation-specific amplification primer or oligonucleotide probe, or between an anucleated blood cells-extracted nucleic acid and a plurality of gene-specific amplification primers or oligonucleotide probes for providing an disease-specific gene expression profile.

DESCRIPTION OF THE DRAWINGS

FIG. 5 shows the probe sequences used for the detection of the genes displayed in FIG. 3C.

DETAILED DESCRIPTION OF THE INVENTION

Figure 1:
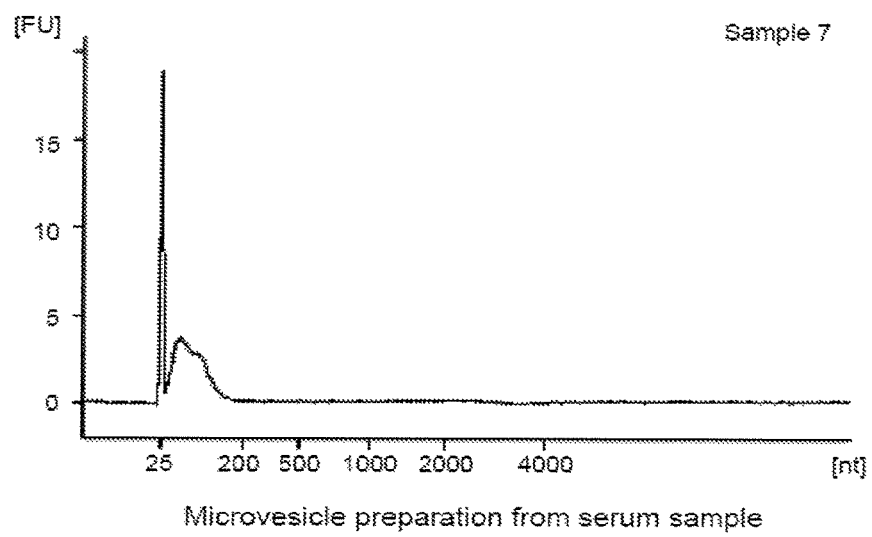
FIG. 1 displays RNA profiles as analyzed using an Agilent Bioanalyzer Picochip (Agilent Technologies, Inc.), with the length of the RNA (in number of nucleotides) on the X-axis, and the amount of RNA (in fluorescence units) on the Y-axis. Here depicted, RNA derived from microvesicles in the blood serum fraction (1A), RNA derived from microvesicles in the blood plasma fraction (1B) or RNA derived from thrombocytes (1C). It is shown that 1) RNA is present in microvesicles in serum and plasma and in thrombocytes, 2) microvesicles isolated from plasma samples contain less RNA than microvesicles isolated from serum samples, and 3) thrombocytes isolated from plasma samples contain RNAs of various sizes, including important fractions of relatively long RNA chains (>200 nucleotides (nt), and even >1000 nucleotides).
Figure 1:
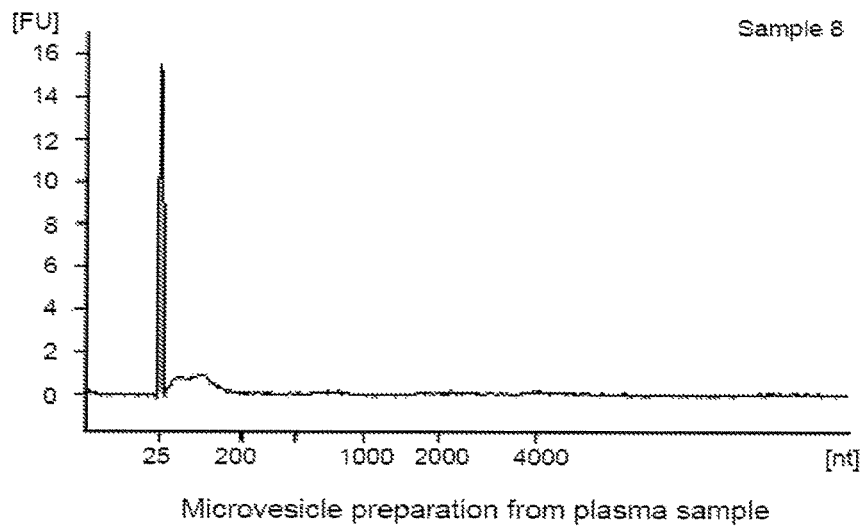
Figure 1:
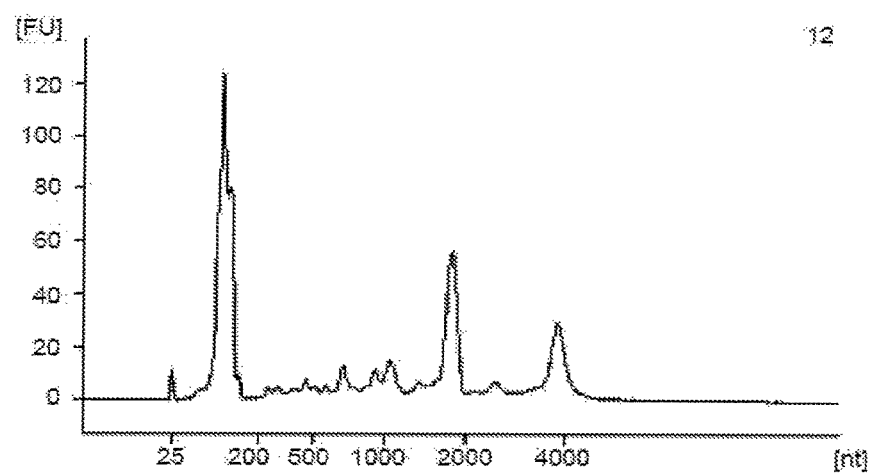
Figure 2:
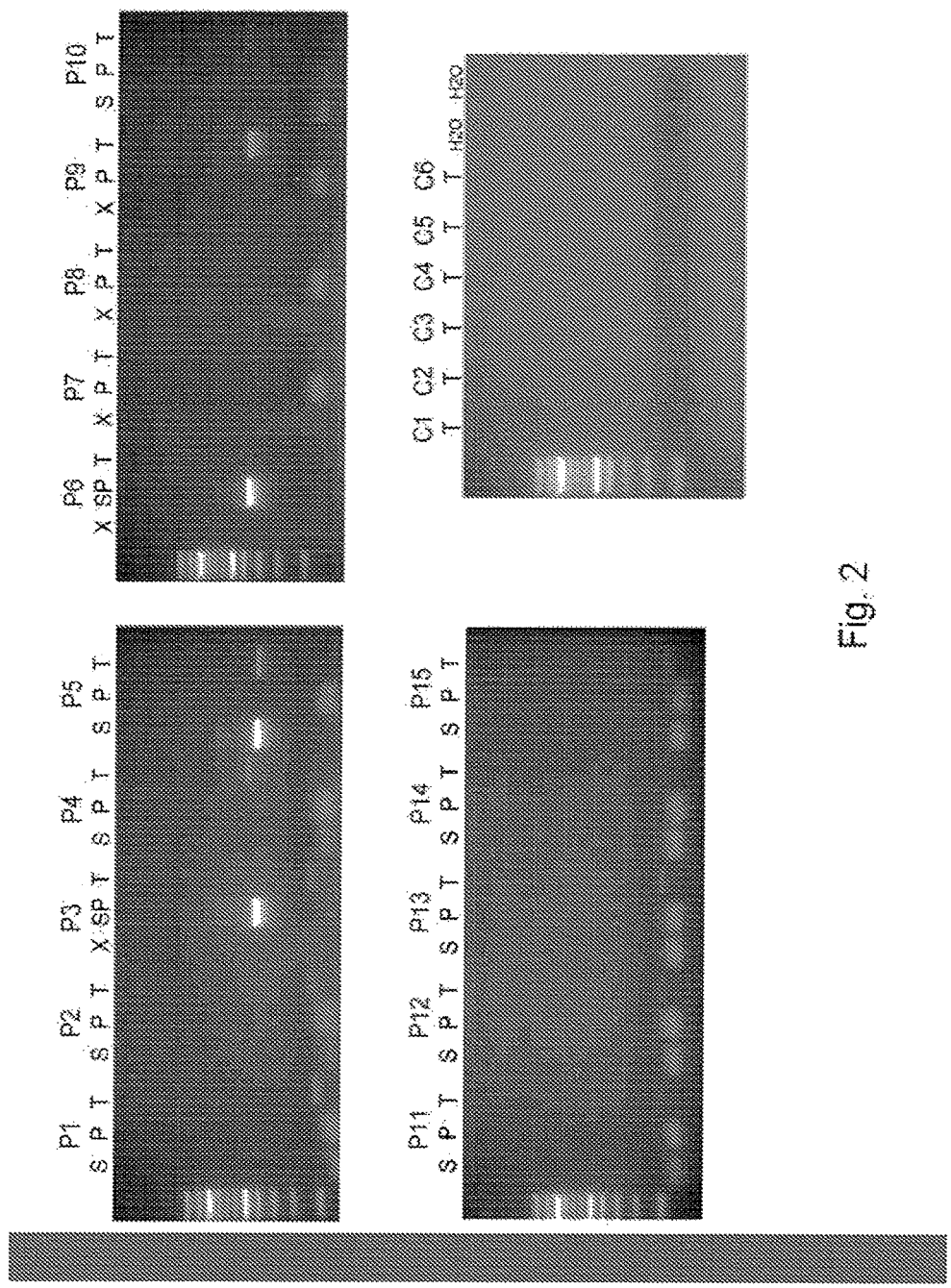
FIG. 2 displays the findings of tumour derived genetic material found in thrombocytes from patients with brain tumours. Blood samples from patients (P1-14) were taken (whole blood tube (serum (S)) and anticoagulant-EDTA blood (plasma (P)). From the plasma tube, thrombocytes (T) were collected by centrifugation protocol. As controls, thrombocytes were collected from healthy individuals ($C_{1-6}$). Some patients lack the serum sample, indicated by X in FIG. 2, and some have pooled serum and plasma samples indicated by SP in FIG. 2. Using nested PCR for RNA detection, the mutant EGFRvIII (V3) could be detected in thrombocytes of 4 glioblastoma patients out of 15 (27%) (P4, P5, P9, P10). This is in line with the published literature where mutant EGFRvIII is found in 20% of high grade gliomas (Liu et al. 2005). These experiments do provide the proof of principle that thrombocytes can be used as a biomarker source for the diagnosis of cancer by the identification of tumour-derived nucleic acids.

As used herein, the term "cancer" refers to a disease or disorder resulting from the proliferation of oncogenically transformed cells. "Cancer" shall be taken to include any one or more of a wide range of benign or malignant tumours, including those that are capable of invasive growth and metastasis through a human or animal body or a part thereof, such as, for example, via the lymphatic system and/or the blood stream. As used herein, the term "tumour" includes both benign and malignant tumours or solid growths, notwithstanding that the present invention is particularly directed to the diagnosis or detection of malignant tumours and solid cancers. Cancers further include but are not limited to carcinomas, lymphomas, or sarcomas, such as, for example, ovarian cancer, colon cancer, breast cancer, pancreatic cancer, lung cancer, prostate cancer, urinary tract cancer, uterine cancer, acute lymphatic leukaemia, Hodgkin's disease, small cell carcinoma of the lung, melanoma, neuroblastoma, glioma (e.g. glioblastoma), and soft tissue sarcoma, lymphoma, melanoma, sarcoma, and adenocarcinoma. In preferred embodiments of aspects of the present invention, thrombocyte cancer is disclaimed.

The term "cancer-derived" as used herein refers to origination from a cancer or cancer cell.

The term "cancer-derived nucleic acid" shall be taken to mean any nucleic acid that is indicative of cancer in the subject, specifically and in most preferred embodiments a mutant DNA or RNA indicating the presence in the cancer of a mutant gene that is expressed by or is present in a cancer cell of the subject, of which mutant gene the nucleic acid sequence is altered relative to the normal gene of a healthy control subject. The term "cancer-derived nucleic acid" shall also be taken to include (i) a nucleic acid that is produced by, expressed by, or present in a cancer cell but not in a normal healthy (non-cancerous) cell, or whose production or expression is altered (enhanced or reduced) by or in a cancer cell compared to a normal cell; or (ii) a nucleic acid that is produced by, expressed by, or present in a normal cell but not by or in a cancer cell. Hence, the nucleic acid need not be a mutant nucleic acid having a mutated sequence but may be a normal nucleic acid having a wild-type (non-cancer) sequence, but whose profile or expression level is altered in a cancer cell relative to a normal cell. In one preferred embodiment, the cancer-derived nucleic acid is a mutant nucleic acid (DNA, cDNA, or RNA) specific for the cancer, preferably an RNA transcript. In another very preferred embodiment, the cancer-derived nucleic acid is a nucleic acid expression profile indicative of being cancer-derived or cancer-specific, as explained in detail herein.

As used herein the term "cancer marker" refers to in particular to a cancer marker gene or a cancer marker gene expression profile. As used herein, the term "cancer marker gene" refers to a gene whose sequence or expression level, alone or in combination with other genes, is correlated with cancer or prognosis of cancer. The correlation may relate to either an increased or decreased expression of the gene reflected in an increased or decreased presence of the RNA expression product of said gene in the nucleic acid fraction obtainable from thrombocytes. For example, the expression of the gene may be indicative of cancer, or lack of expression of the gene may be correlated with poor prognosis in a cancer patient. In the case of prostate cancer AMACR, PCA3 and PSA are suitable cancer markers. In the case of colorectal cancer KRAS mutations are suitable cancer markers. In the case of lung carcinoma EGFR mutations are suitable cancer markers. In the case of melanoma BRAF mutations are suitable cancer markers. In the case of glioma EGFRvIII mutations are suitable cancer markers. Other suitable cancer markers may be derived from Tables 1 and 2 as provided herein or from the Examples or Figures. The skilled person will understand that many other cancer markers may be employed in aspects and embodiments of this invention.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

The term "cancer" in the terms "cancer derived", "cancer marker", "cancer marker gene", and/or "stage of cancer" may be generalized to the term "disease" as the definitions for cancer are generally applicable to all diseases as indicated herein.

The term "disease-derived" as used herein refers to origination from a disease or diseased cell.

The term "disease-derived nucleic acid" shall be taken to mean any nucleic acid that is indicative of a disease in the subject, specifically and in most preferred embodiments a mutant DNA or RNA indicating the presence in the disease of a mutant gene that is expressed by or is present in a diseased cell of the subject, of which mutant gene the nucleic acid sequence is altered relative to the normal gene of a healthy control subject. The term "disease-derived nucleic acid" shall also be taken to include (i) a nucleic acid that is produced by, expressed by, or present in a diseased cell but not in a normal healthy (non-diseased) cell, or whose production or expression is altered (enhanced or reduced) by or in a diseased cell compared to a normal cell; or (ii) a nucleic acid that is produced by, expressed by, or present in a normal cell but not by or in a diseased cell. Hence, the nucleic acid need not be a mutant nucleic acid having a mutated sequence but may be a normal nucleic acid having a wild-type (non-disease) sequence, but whose profile or expression level is altered in a diseased cell relative to a normal cell. In one preferred embodiment, the disease-derived nucleic acid is a mutant nucleic acid (DNA, cDNA, or RNA) specific for the disease, preferably an RNA transcript. In another very preferred embodiment, the disease-derived nucleic acid is a nucleic acid expression profile indicative of being disease-derived or disease-specific, as explained in detail herein. In a preferred embodiment disease-derived nucleic acid does not include cancer-derived nucleic acid. In yet another preferred embodiment, the disease derived nucleic acid does not include vascular disease derived nucleic acid, and/or systemic lupus erythematosus derived nucleic acid. In a preferred embodiment disease-derived nucleic acid does not include sickle cell disease derived nucleic acid. In a preferred embodiment disease-derived nucleic acid does not include Alzheimer's disease derived nucleic acid. In a preferred embodiment of the present invention and embodiments thereof the disease-derived nucleic acid does not include CD109 nucleic acid. In yet another preferred embodiment of the present invention and embodiments thereof, the disease-derived nucleic acid does not comprise megakaryocyte derived nucleic acid. In yet another preferred embodiment of the present invention and embodiments thereof, the disease-derived nucleic acid does not comprise nucleic acid derived from disease associated with pathological megakaryocyte and/or platelet function.

As used herein the term "disease marker" refers to in particular to a disease marker gene or a disease marker gene expression profile. As used herein, the term "disease marker gene" refers to a gene whose sequence or expression level, alone or in combination with other genes, is correlated with disease or prognosis of the disease. The correlation may relate to either an increased or decreased expression of the gene reflected in an increased or decreased presence of the RNA expression product of said gene in the nucleic acid fraction obtainable from thrombocytes. For example, the expression of the gene may be indicative of a disease, or lack of expression of the gene may be correlated with poor prognosis in a patient. In a preferred embodiment said disease marker gene is not a CD109 gene.

As used herein, the term "stage of disease" refers to a qualitative or quantitative assessment of the level of advancement of a disease. Criteria used to determine the stage of a disease include, but are not limited to, whether the disease has spread to other parts of the body and where the disease has spread to (e.g., within the same organ or region of the body or to another organ).

The term "disease" as used herein may refer to cancer, autoimmune disease, skin diseases, eye disease, endocrine diseases, neurological disorders, and cardiovascular diseases.

The term "disease" as used herein may refer to autoimmune disease, skin diseases, eye disease, endocrine diseases, neurological disorders, and/or cardiovascular diseases.

The term "disease" as used herein may refer to autoimmune disease, skin diseases, eye disease, endocrine diseases, and/or neurological disorders.

The term "disease" as used herein may, in some preferred embodiments, not refer to cancer, cardiovascular disease, systemic lupus erythematosus, sickle cell disease, Alzheimer's disease, diseases associated with pathological platelet function, and/or diseases associated with pathological megakaryocyte function.

Thus, diseases that in addition to or instead of cancer can be detected using the means and methods of the present invention include for instance the following auto-immune diseases: Achlorhydra Autoimmune Active Chronic Hepatitis; Acute Disseminated Encephalomyelitis; Acute hemorrhagic leukoencephalitis; Addison's Disease; Agammaglobulinemia; Alopecia greata; Amyotrophic Lateral Sclerosis; Ankylosing Spondylitis; Anti-GBM/TBM Nephritis; Antiphospholipid syndrome; Antisynthetase syndrome; polyarticular Arthritis; Atopic allergy; Atopic Dermatitis; Autoimmune Aplastic Anemia; Autoimmune cardiomyopathy; Autoimmune enteropathy; Autoimmune hemolytic anemia; Autoimmune hepatitis; Autoimmune inner ear disease; Autoimmune lymphoproliferative syndrome; Autoimmune peripheral neuropathy; Autoimmune pancreatitis; Autoimmune polyendocrine syndrome; Autoimmune progesterone dermatitis; Autoimmune thrombocytopenic purpura; Autoimmune uveitis; Balo disease/Balo concentric sclerosis; Bechets Syndrome; Berger's disease; Bickerstaffs encephalitis; Blau syndrome; Bullous Pemphigoid; Castleman's disease; Celiac disease; Chagas disease; Chronic Fatigue Immune Dysfunction Syndrome; Chronic inflammatory demyelinating polyneuropathy; Chronic recurrent multifocal osteomyelitis; Chronic lyme disease; Chronic obstructive pulmonary disease; Churg-Strauss syndrome; Cicatricial Pemphigoid; Coeliac Disease; Cogan syndrome; Cold agglutinin disease; Complement component 2 deficiency; Cranial arteritis; CREST syndrome; Crohns Disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Dressler's syndrome; Discoid lupus erythematosus; Eczema; Endometriosis; Enthesitis-related arthritis; Eosinophilic fasciitis; Eosinophilic gastroenteritis; Epidermolysis bullosa acquisita; Erythema nodosum; Essential mixed cryoglobulinemia; Evan's syndrome; Fibrodysplasia ossificans progressiva; Fibromyalgia/Fibromyositis; Fibrosing aveolitis; Gastritis; Gastrointestinal pemphigoid; Giant cell arteritis; Glomerulonephritis; Goodpasture's syndrome; Graves' disease; Guillain-Barré syndrome; Hashimoto's encephalitis; Hashimoto's thyroiditis; Haemolytic anaemia; Henoch-Schonlein purpura; Herpes gestationis; Hidradenitis suppurativa; Hughes syndrome; Hypogammaglobulinemia; Idiopathic Inflammatory Demyelinating Diseases; Idiopathic pulmonary fibrosis; Idiopathic thrombocytopenic purpura; IgA nephropathy; Inclusion body myositis; Inflammatory demyelinating polyneuopathy; Interstitial cystitis; Irritable Bowel Syndrome (IBS); Juvenile idiopathic arthritis; Juvenile rheumatoid arthritis; Kawasaki's Disease; Lambert-Eaton myasthenic syndrome; Leukocytoclastic vasculitis; Lichen planus; Lichen sclerosus; Linear IgA disease; Lou Gehrig's Disease; Lupoid hepatitis; Lupus erythematosus; Majeed syndrome; Ménière's disease; Microscopic polyangiitis; Miller-Fisher syndrome; Mixed Connective Tissue Disease; Morphea; Mucha-Habermann disease; Muckle-Wells syndrome; Multiple Myeloma; Multiple Sclerosis; Myasthenia gravis; Myositis; Narcolepsy; Neuromyelitis optica; Neuromyotonia; Occular cicatricial pemphigoid; Opsoclonus myoclonus syndrome; Ord thyroiditis; Palindromic rheumatism; PANDAS; Paraneoplastic cerebellar degeneration; Paroxysmal nocturnal hemoglobinuria; Parry Romberg syndrome; Parsonnage-Turner syndrome; Pars planitis; Pemphigus; Pemphigus vulgaris; Pernicious anaemia; Perivenous encephalomyelitis; POEMS syndrome; Polyarteritis nodosa; Polymyalgia rheumatica; Polymyositis; Primary biliary cirrhosis; Primary sclerosing cholangitis; Progressive inflammatory neuropathy; Psoriasis; Psoriatic Arthritis; Pyoderma gangrenosum; Pure red cell aplasia; Rasmussen's encephalitis; Raynaud phenomenon; Relapsing polychondritis; Reiter's syndrome; Restless leg syndrome; Retroperitoneal fibrosis; Rheumatoid arthritis; Rheumatoid fever; Sarcoidosis; Schizophrenia; Schmidt syndrome; Schnitzler syndrome; Scleritis; Scleroderma; Sjögren's syndrome; Spondyloarthropathy; Sticky blood syndrome; Still's Disease; Stiff person syndrome; Subacute bacterial endocarditis (SBE); Susac's syndrome; Sweet syndrome; Sydenham Chorea; Sympathetic ophthalmia; Takayasu's arteritis; Temporal arteritis; Tolosa-Hunt syndrome; Transverse Myelitis; Ulcerative Colitis; Undifferentiated connective tissue disease; Undifferentiated spondyloarthropathy; Vasculitis; Vitiligo; Wegener's granulomatosis; Wilson's syndrome; and Wiskott-Aldrich syndrome.

Apart from the above diseases, aspects of the present invention are also applicable to the prognosis and diagnosis of the following skin diseases: Acneiform eruptions; Autoinflammatory syndromes; Chronic blistering; Conditions of the mucous membranes; Conditions of the skin appendages; Conditions of the subcutaneous fat; Congenital anomalies; Connective tissue diseases (such as Abnormalities of dermal fibrous and elastic tissue); Dermal and subcutaneous growths; Dermatitis (including Atopic Dermatitis, Contact Dermatitis, Eczema, Pustular Dermatitis, and Seborrheic Dermatitis); Disturbances of pigmentation; Drug eruptions; Endocrine-related skin disease; Eosinophilic; Epidermal nevi, neoplasms, cysts; Erythemas; Genodermatoses; Infection-related skin disease; Lichenoid eruptions; Lymphoid-related skin disease; Melanocytic nevi and neoplasms (including Melanoma); Monocyte- and macrophage-related skin disease; Mucinoses; Neurocutaneous; Noninfectious immunodeficiency-related skin disease; Nutrition-related skin disease; Papulosquamous hyperkeratotic (including Palmoplantar keratodermas); Pregnancy-related skin disease; Pruritic; Psoriasis; Reactive neutrophilic; Recalcitrant palmoplantar eruptions; Resulting from errors in metabolism; Resulting from physical factors (including Ionizing radiation-induced); Urticaria and angioedema; Vascular-related skin disease.

Apart from the above diseases, aspects of the present invention are also applicable to the prognosis and diagnosis of the following endocrine diseases: Adrenal disorders; Glucose homeostasis disorders; Thyroid disorders; Calcium homeostasis disorders and Metabolic bone disease; Pituitary gland disorders; and Sex hormone disorders.

Apart from the above diseases, aspects of the present invention are also applicable to the prognosis and diagnosis of the following eye diseases: H00-H06 Disorders of eyelid, lacrimal system and orbit; H10-H13 Disorders of conjunctiva; H15-H22 Disorders of sclera, cornea, iris and ciliary body; H25-H28 Disorders of lens; H30-H36 Disorders of choroid and retina (including H30 Chorioretinal inflammation, H31 Other disorders of choroid, $H_{32}$Chorioretinal disorders in diseaseas classified elsewhere, H33 Retinal detachments and breaks, H34 Retinal vascular occlusions, H35 Other retinal disorders, and H36 Retinal disorders in diseases classified elsewhere); H40-H42 Glaucoma; H43-H45 Disorders of vitreous body and globe; H46-H48 Disorders of optic nerve and visual pathways; H49-H52 Disorders of ocular muscles, binocular movement, accommodation and refraction; H53-H54.9 Visual disturbances and blindness; and H55-H59 Other disorders of eye and adnexa.

Apart from the above diseases, aspects of the present invention are also applicable to the prognosis and diagnosis of the following neurological disorders: Abarognosis; Acquired Epileptiform Aphasia; Acute disseminated encephalomyelitis; Adrenoleukodystrophy; Agenesis of the corpus callosum; Agnosia; Aicardi syndrome; Alexander disease; Alien hand syndrome; Allochiria; Alpers' disease; Alternating hemiplegia; Alzheimer's disease; Amyotrophic lateral sclerosis (see Motor Neurone Disease); Anencephaly; Angelman syndrome; Angiomatosis; Anoxia; Aphasia; Apraxia; Arachnoid cysts; Arachnoiditis; Arnold-Chiari malformation; Arteriovenous malformation; Ataxia Telangiectasia; Attention deficit hyperactivity disorder; Auditory processing disorder; Autonomic Dysfunction; Back Pain; Batten disease; Behcet's disease; Bell's palsy; Benign Essential Blepharospasm; Benign Intracranial Hypertension; Bilateral frontoparietal polymicrogyria; Binswanger's disease; Blepharospasm; Bloch-Sulzberger syndrome; Brachial plexus injury; Brain abscess; Brain damage; Brain injury; Brain tumor; Brown-Séquard syndrome; Canavan disease; Carpal tunnel syndrome; Causalgia; Central pain syndrome; Central pontine myelinolysis; Centronuclear myopathy; Cephalic disorder; Cerebral aneurysm; Cerebral arteriosclerosis; Cerebral atrophy; Cerebral gigantism; Cerebral palsy; Cerebral vasculitis; Cervical spinal stenosis; Charcot-Marie-Tooth disease; Chiari malformation; Chorea; Chronic fatigue syndrome; Chronic inflammatory demyelinating polyneuropathy (CIDP); Chronic pain; Coffin Lowry syndrome; Coma; Complex regional pain syndrome; Compression neuropathy; Congenital facial diplegia; Corticobasal degeneration; Cranial arteritis; Craniosynostosis; Creutzfeldt-Jakob disease; Cumulative trauma disorders; Cushing's syndrome; Cytomegalic inclusion body disease (CIBD); Cytomegalovirus Infection; Dandy-Walker syndrome; Dawson disease; De Morsier's syndrome; Dejerine-Klumpke palsy; Dejerine-Sottas disease; Delayed sleep phase syndrome; Dementia; Dermatomyositis; Developmental dyspraxia; Diabetic neuropathy; Diffuse sclerosis; Dravet syndrome; Dysautonomia; Dyscalculia; Dysgraphia; Dyslexia; Dystonia; Empty sella syndrome; Encephalitis; Encephalocele; Encephalotrigeminal angiomatosis; Encopresis; Epilepsy; Erb's palsy; Erythromelalgia; Essential tremor; Fabry's disease; Fahr's syndrome; Fainting; Familial spastic paralysis; Febrile seizures; Fisher syndrome; Friedreich's ataxia; Fibromyalgia; Gaucher's disease; Gerstmann's syndrome; Giant cell arteritis; Giant cell inclusion disease; Globoid Cell Leukodystrophy; Gray matter heterotopia; Guillain-Barré syndrome; HTLV-1 associated myelopathy; Hallervorden-Spatz disease; Head injury; Headache; Hemifacial Spasm; Hereditary Spastic Paraplegia; Heredopathia atactica polyneuritiformis; Herpes zoster oticus; Herpes zoster; Hirayama syndrome; Holoprosencephaly; Huntington's disease; Hydranencephaly; Hydrocephalus; Hypercortisolism; Hypoxia; Immune-Mediated encephalomyelitis; Inclusion body myositis; Incontinentia pigmenti; Infantile phytanic acid storage disease; Infantile Refsum disease; Infantile spasms; Inflammatory myopathy; Intracranial cyst; Intracranial hypertension; Joubert syndrome; Karak syndrome; Kearns-Sayre syndrome; Kennedy disease; Kinsbourne syndrome; Klippel Feil syndrome; Krabbe disease; Kugelberg-Welander disease; Kuru; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Lewy body dementia; Lissencephaly; Locked-In syndrome; Lou Gehrig's disease (See Motor Neurone Disease); Lumbar disc disease; Lumbar spinal stenosis; Lyme disease—Neurological Sequelae; Machado-Joseph disease (Spinocerebellar ataxia type 3); Macrencephaly; Macropsia; Megalencephaly; Melkersson-Rosenthal syndrome; Menieres disease; Meningitis; Menkes disease; Metachromatic leukodystrophy; Microcephaly; Micropsia; Migraine; Miller Fisher syndrome; Mini-stroke (transient ischemic attack); Mitochondrial myopathy; Mobius syndrome; Monomelic amyotrophy; Motor Neurone Disease; Motor skills disorder; Moyamoya disease; Mucopolysaccharidoses; Multi-infarct dementia; Multifocal motor neuropathy; Multiple sclerosis; Multiple system atrophy; Muscular dystrophy; Myalgic encephalomyelitis; Myasthenia gravis; Myelinoclastic diffuse sclerosis; Myoclonic Encephalopathy of infants; Myoclonus; Myopathy; Myotubular myopathy; Myotonia congenita; Narcolepsy; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Niemann-Pick disease; Non 24-hour sleep-wake syndrome; Nonverbal learning disorder; O'Sullivan-McLeod syndrome; Occipital Neuralgia; Occult Spinal Dysraphism Sequence; Ohtahara syndrome; Olivopontocerebellar atrophy; Opsoclonus myoclonus syndrome; Optic neuritis; Orthostatic Hypotension; Overuse syndrome; Palinopsia; Paresthesia; Parkinson's disease; Paramyotonia Congenita; Paraneoplastic diseases; Paroxysmal attacks; Parry-Romberg syndrome; Pelizaeus-Merzbacher disease; Periodic Paralyses; Peripheral neuropathy; Persistent Vegetative State; Pervasive developmental disorders; Photic sneeze reflex; Phytanic acid storage disease; Pick's disease; Pinched nerve; Pituitary tumors; PMG; Polio; Polymicrogyria; Polymyositis; Porencephaly; Post-Polio syndrome; Postherpetic Neuralgia (PHN); Postinfectious Encephalomyelitis; Postural Hypotension; Prader-Willi syndrome; Primary Lateral Sclerosis; Prion diseases; Progressive hemifacial atrophy; Progressive multifocal leukoencephalopathy; Progressive Supranuclear Palsy; Pseudotumor cerebri; Rabies; Ramsay-Hunt syndrome (Type I and Type II); Rasmussen's encephalitis; Reflex neurovascular dystrophy; Refsum disease; Repetitive motion disorders; Repetitive stress injury; Restless legs syndrome; Retrovirus-associated myelopathy; Rett syndrome; Reye's syndrome; Rhythmic Movement Disorder; Romberg syndrome; Saint Vitus dance; Sandhoff disease; Schizophrenia; Schilder's disease; Schizencephaly; Sensory integration dysfunction; Septo-optic dysplasia; Shaken baby syndrome; Shingles; Shy-Drager syndrome; Sjögren's syndrome; Sleep apnea; Sleeping sickness; Snatiation; Sotos syndrome; Spasticity; Spina bifida; Spinal cord injury; Spinal cord tumors; Spinal muscular atrophy; Spinocerebellar ataxia; Steele-Richardson-Olszewski syndrome; Stiff-person syndrome; Stroke; Sturge-Weber syndrome; Subacute sclerosing panencephalitis; Subcortical arteriosclerotic encephalopathy; Superficial siderosis; Sydenham's chorea; Syncope; Synesthesia; Syringomyelia; Tarsal tunnel syndrome; Tardive dyskinesia; Tarlov cyst; Tay-Sachs disease; Temporal arteritis; Tetanus; Tethered spinal cord syndrome; Thomsen disease; Thoracic outlet syndrome; Tic Douloureux; Todd's paralysis; Tourette syndrome; Toxic encephalopathy; Transient ischemic attack; Transmissible spongiform encephalopathies; Transverse myelitis; Traumatic brain injury; Tremor; Trigeminal neuralgia; Tropical spastic paraparesis; Trypanosomiasis; Tuberous sclerosis; Von Hippel-Lindau disease; Viliuisk Encephalomyelitis; Wallenberg's syndrome; Werdnig-Hoffman disease; West syndrome; Whiplash; Williams syndrome; Wilson's disease; and Zellweger syndrome.

Apart from the above diseases, aspects of the present invention are also applicable to the prognosis and diagnosis of the following cardiovascular diseases: Aneurysm; Angina; Atherosclerosis; Cerebrovascular Accident (Stroke); Cerebrovascular disease; Congestive Heart Failure; Coronary Artery Disease; Myocardial infarction (Heart Attack); and Peripheral vascular disease. In a preferred embodiment of the method of the invention and embodiments thereof, and in preferred embodiments of other aspects of the invention, the disease or the cardiovascular disease is not systemic lupus erythematosus.

In a preferred embodiment of the method of the invention and embodiments thereof, and in preferred embodiments of other aspects of the invention, the disease is not a disease selected from the group comprising cancer, cardiovascular disease, systemic lupus erythematosus, sickle cell disease, Alzheimer's disease, diseases associated with pathological platelet function, and/or diseases associated with pathological megakaryocyte function.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "RNA" refers to ribonucleic acid, a molecule of RNA encoding for a protein product or non-coding for a protein product (such as miRNAs but not excluding other non-coding RNAs). RNA is transcribed from a DNA template.

As used herein the term "mutant" refers to a nucleic acid compound, protein, molecule, vector or cell resulting from mutation of the native wild type coding sequence or subunits thereof.

As used herein the term "mutation" refers to any change that alters a native coding sequence either by displacement, addition, deletion, insertion, cross-linking, or other destruction or substitution of one or more nucleotides of the native coding sequence, including naturally occurring splice variants. In particular, the mutation provides a gene that causes the cell to be a cancer cell. Such mutations include inherited and acquired mutations of tumor suppressor genes and/or oncogenes.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology. Principles and Applications, D. H. Persing et al., Ed., American Society for Microbiology, Washington, D.C. (1993). The product of amplification is termed an amplicon.

The term "hybrid" refers to a double-stranded nucleic acid molecule, or duplex, formed by hydrogen bonding between complementary nucleotides. The terms "hybridise" or "anneal" refer to the process by which single strands of nucleic acid sequences form double-helical segments through hydrogen bonding between complementary nucleotides.

The term "oligonucleotide" refers to a short sequence of nucleotide monomers (usually 6 to 100 nucleotides) joined by phosphorous linkages (e.g., phosphodiester, alkyl and aryl-phosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in PCR amplification.

The term "probe" refers to a single-stranded oligonucleotide sequence that will recognize and form a hydrogen-bonded duplex with a complementary sequence in a target nucleic acid sequence analyte or its cDNA derivative.

The terms "stringency" or "stringent hybridization conditions" refer to hybridization conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridises to a perfectly matched probe or primer. Typically, stringent conditions will be those in which the salt concentration is less than about 1.0 M Na$^+$ ion, typically about 0.01 to 1.0 M Na$^+$ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C.

Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

"Subject" as used herein includes, but is not limited to, mammals, including, e.g., a human, a non-human primate, a mouse, a pig, a cow, a goat, a cat, a rabbit, a rat, a guinea pig, a hamster, a degu, a horse, a monkey, a sheep, or other non-human mammal; and non-mammal animals, including, e.g., a non-mammalian vertebrate, such as a bird (e.g., a chicken or duck) or a fish, and an invertebrate. The subject may be a healthy animal or human subject undergoing a routine well-being check up. Alternatively, the subject may be at risk of having a disease (e.g., a genetically predisposed subject, a subject with medical and/or family history of cancer, a subject who has been exposed to carcinogens, occupational hazard, environmental hazard] and/or a subject who exhibits suspicious clinical signs of a disease [e.g., blood in the stool or melena, unexplained pain, sweating, unexplained fever, unexplained loss of weight up to anorexia, changes in bowel habits (constipation and/or diarrhoea), tenesmus (sense of incomplete defecation, for rectal cancer specifically), anaemia and/or general weakness). According to another embodiment, the subject may be a patient diagnosed with the disease and is performing a routine check-up, in-between treatments.

The term "thrombocyte", as used herein, refers to blood platelets, i.e. the small, irregularly-shaped cell fragments that do not have a nucleus containing DNA, and that circulate in the blood of mammals. Thrombocytes are 2-3 µm in diameter, and are derived from fragmentation of precursor megakaryocytes. Platelets or thrombocytes lack nuclear DNA, although they retain some megakaryocyte-derived mRNAs as part of their lineal origin. The average lifespan of a thrombocyte is 5 to 9 days. Thrombocytes are involved and play an essential role in haemostasis, leading to the formation of blood clots. In a preferred embodiment of the present invention and embodiments thereof, the anucleated blood cell-extracted nucleic acid fraction is not megakaryocyte-derived nucleic acid or megakaryocyte-derived RNA.

The term "blood" as used herein refers to whole blood (including plasma and cells) and includes arterial, capillary and venous blood.

The term "nucleated cell" as used herein preferably refers to a Bartholin's gland cell; Salivary gland mucous cell; Salivary gland serous cell; Von Ebner's gland cell; Mammary gland cell; Lacrimal gland cell; Ceruminous gland cell; Eccrine sweat gland cell; Apocrine sweat gland cell; Gland of Moll cell; Sebaceous gland cell; Bowman's gland cell; Brunner's gland cell; Seminal vesicle cell; Prostate gland cell; Bulbourethral gland cell; Gland of Littre cell; Uterus endometrium cell; Isolated goblet cell; Stomach lining mucous cell; Gastric gland zymogenic cell; Gastric gland oxyntic cell; Pancreatic acinar cell; Paneth cell; Type II pneumocyte; Clara cell; Anterior pituitary cell; Intermediate pituitary cell; Magnocellular neurosecretory cell; Thyroid gland cell; Parathyroid gland cells; Adrenal gland cells; Leydig cell; Theca interna cell; Corpus luteum cell; Juxtaglomerular cell; Macula densa cell; Peripolar cell; Mesangial cell; Blood vessel and lymphatic vascular endothelial fenestrated cell; Blood vessel and lymphatic vascular endothelial continuous cell; Blood vessel and lymphatic vascular endothelial splenic cell; Synovial cell; Serosal cell; Squamous cell; Columnar cell; Dark cell; Vestibular membrane cell; Stria vascularis basal cell; Stria vascularis marginal cell; Cell of Claudius; Cell of Boettcher; Choroid plexus cell; Pia-arachnoid squamous cell; Pigmented ciliary epithelium cell; Nonpigmented ciliary epithelium cell; Corneal endothelial cell; Peg cell; Respiratory tract ciliated cell; Oviduct ciliated cell; Uterine endometrial ciliated cell; Rete testis ciliated cell; Ductulus efferens ciliated cell; Ciliated ependymal cell; Epidermal keratinocyte; Epidermal basal cell; Keratinocyte; Nail bed basal cell; Medullary hair shaft cell; Cortical hair shaft cell; Cuticular hair shaft cell; Cuticular hair root sheath cell; External hair root sheath cell; Hair matrix cell; Surface epithelial cell; basal cell; Urinary epithelium cell; Auditory inner hair cell; Auditory outer hair cell; Primary sensory neurons; Merkel cell; Olfactory receptor neuron; Photoreceptor cells; Carotid body cell (blood pH sensor); Hair cell; Taste bud cell; Cholinergic neural cell; Adrenergic neural cell; Peptidergic neural cell; Inner pillar cell; Outer pillar cell; Inner phalangeal cell; Outer phalangeal cell; Border cell; Hensen cell; Vestibular apparatus supporting cell; Taste bud supporting cell; Olfactory epithelium supporting cell; Schwann cell; Satellite cell; Enteric glial cell; Astrocyte; Neuron cells; Oligodendrocyte; Spindle neuron; Anterior lens epithelial cell; Crystallin-containing lens fiber cell; Hepatocyte; Adipocytes; Liver lipocyte; Kidney glomerulus parietal cell; Kidney glomerulus podocyte; Kidney proximal tubule brush border cell; Loop of Henle thin segment cell; Kidney distal tubule cell; Kidney collecting duct cell; pneumocyte; Pancreatic duct cell; Nonstriated duct cell; Duct cell; Intestinal brush border cell; Exocrine gland striated duct cell; Gall bladder epithelial cell; Ductulus efferens nonciliated cell; Epididymal principal cell; Epididymal basal cell; Ameloblast epithelial cell; Planum semilunatum epithelial cell; Organ of Corti interdental epithelial cell; Loose connective tissue fibroblasts; Corneal fibroblasts; Tendon fibroblasts; Bone marrow reticular tissue fibroblasts; Other nonepithelial fibroblasts; Pericyte; Nucleus pulposus cell; Cementoblast/cementocyte; Odontoblast/odontocyte; Hyaline cartilage chondrocyte; Fibrocartilage chondrocyte; Elastic cartilage chondrocyte; Osteoblast/osteocyte; Osteoprogenitor cell; Hyalocyte; Stellate cell; Hepatic stellate cell; Pancreatic stelle cell; Skeletal muscle cell; Satellite cell; Heart muscle cell; Smooth muscle cell; Myoepithelial cell; Monocyte; Connective tissue macrophage; Epidermal Langerhans cell; Osteoclast; Dendritic cell; Microglial cell; Neutrophil granulocyte; Eosinophil granulocyte; Basophil granulocyte; Mast cell; Helper T cell; Suppressor T cell; Cytotoxic T cell; Natural Killer T cell; B cell; Natural killer cell; Reticulocyte; Melanocyte; Retinal pigmented epithelial cell; Oogonium/Oocyte; Spermatid; Spermatocyte; Spermatogonium cell; Spermatozoon; Ovarian follicle cell; Sertoli cell; Thymus epithelial cell; and Interstitial kidney cell.

Targeted therapy and personalized medicine are critically depending on disease profiling and the development of companion diagnostics. Mutations in disease-derived nucleic acids can be highly predictive for the response to targeted treatment. However, obtaining easily accessible high-quality nucleic acids remains a significant developmental hurdle. Blood generally contains 150,000-350,000 thrombocytes (platelets) per microliter, providing a highly available biomarker source for research and clinical use. Moreover, thrombocyte isolation is relatively simple and is a standard procedure in blood bank/haematology labs. Since platelets do not contain a nucleus, their RNA transcripts—needed for functional maintenance—are derived from bone marrow megakaryocytes during thrombocyte origination. It has now been found that thrombocytes may take up RNA and/or DNA from cells other than megakaryocytes during circulation via various transfer mechanisms. Tumor cells for instance release an abundant collection of genetic material, some of which is secreted by microvesicles in the form of mutant RNA. During circulation in the blood stream thrombocytes absorb the genetic material secreted by cancer cells and other diseased cells, serving as an attractive platform for the companion diagnostics of cancer and other diseases as indicated above e.g. in the context of personalized medicine.

In the Examples below it is shown that platelets isolated from healthy human control subjects have the ability to take up RNA from RNA-containing microvesicles derived from human brain tumor cells (glioma), after which they contain tumor-associated RNA, including for instance mutant EGFRvIII mRNA in the case of glioma patients. Hence, it was determined that circulating platelets isolated from glioma patients contain RNA biomarkers. RT-PCR was used to confirm that mutant EGFRvIII mRNA found in the thrombocytes reflects the presence of glioma tissues.

The presence of tumor and/or disease-markers messages is not unique to platelets from glioma patients but is more generally applicable for a wide range of diseases as identified herein. Messenger RNAs coding for the prostate cancer markers PCA3 and PSA could be demonstrated in platelets from prostate cancer patients, whereas these markers were absent in platelets from healthy control subjects.

Figure 3A:
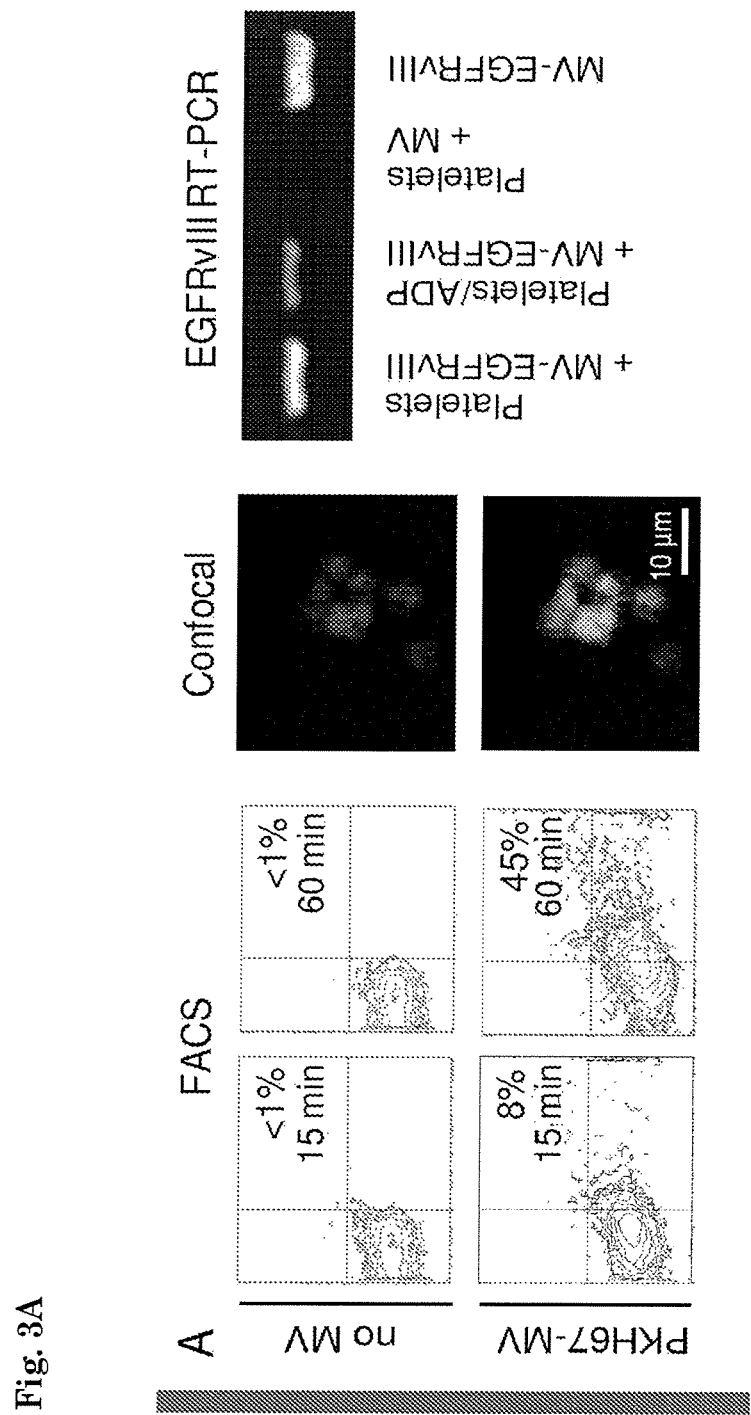
FIG. 3. (A) U87 glioma-derived microvesicles were labelled with PKH67 green fluorescent dye and incubated with isolated platelets. After 15 and 60 min of incubation in the presence and absence of microvesicles the platelets were washed and subjected to FACS analysis of PKH67 fluorescence. In addition, the platelets were stained and analyzed by confocal microscopy to determine microvesicle uptake. RNA was isolated from RNase-treated platelets after incubation with microvesicles under different conditions. RT-PCR was performed to detect EGFRvIII RNA. MV/MVEGFRvIII: microvesicles isolated from U87/U87-EGFRvIII cells. (B) RNA was isolated from platelets from healthy control subjects or glioma patients and subjected to RT-PCR analysis. Corresponding glioma tissue biopsies served as control. PC=U87-EGFRvIII RNA; NC=H20; nd=not determined; * indicates positive signal. (C) RNA as in (B) was subjected to gene expression arrays. Heat map of top-30 glioma biomarkers is shown on the left. Individual expression levels for the top-10 RNAs depicted on the right. Dashed line=BG (background).
Figure 3B:
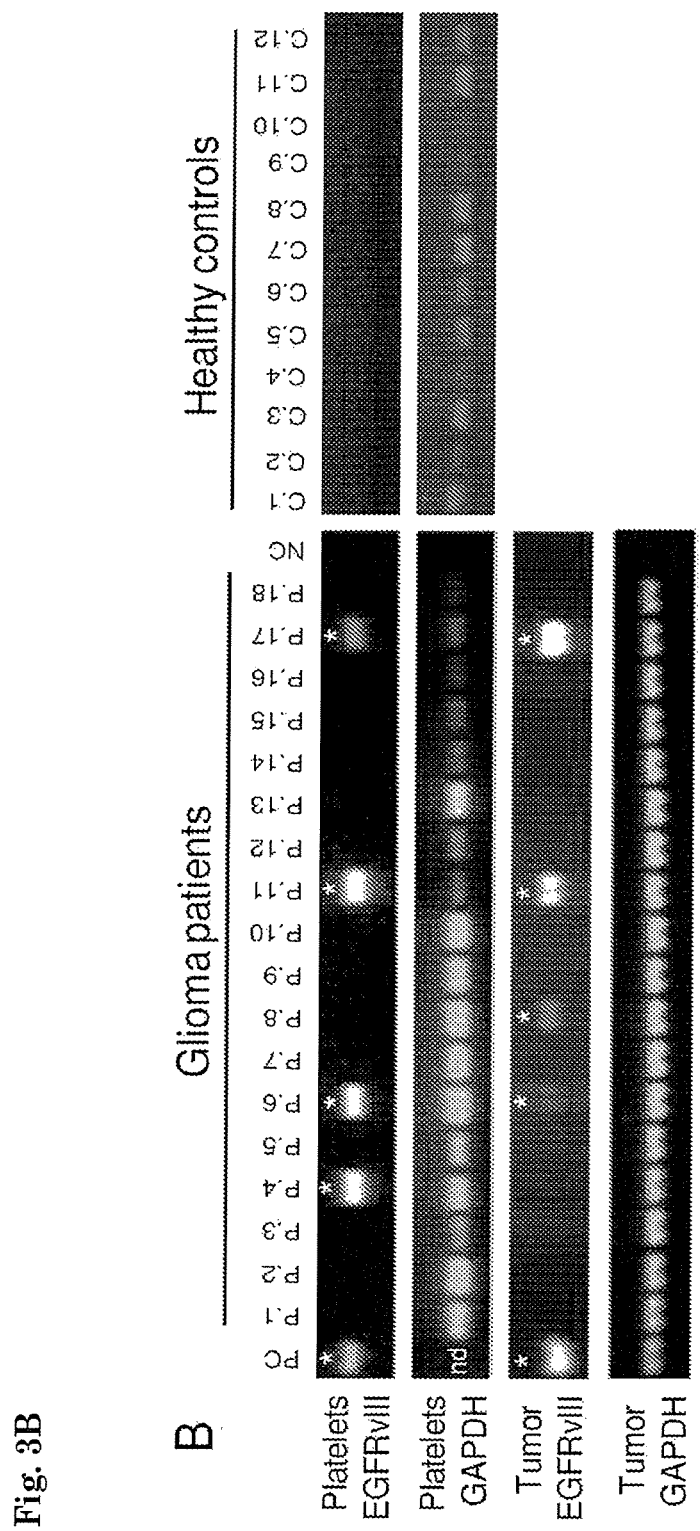
Figure 3C:
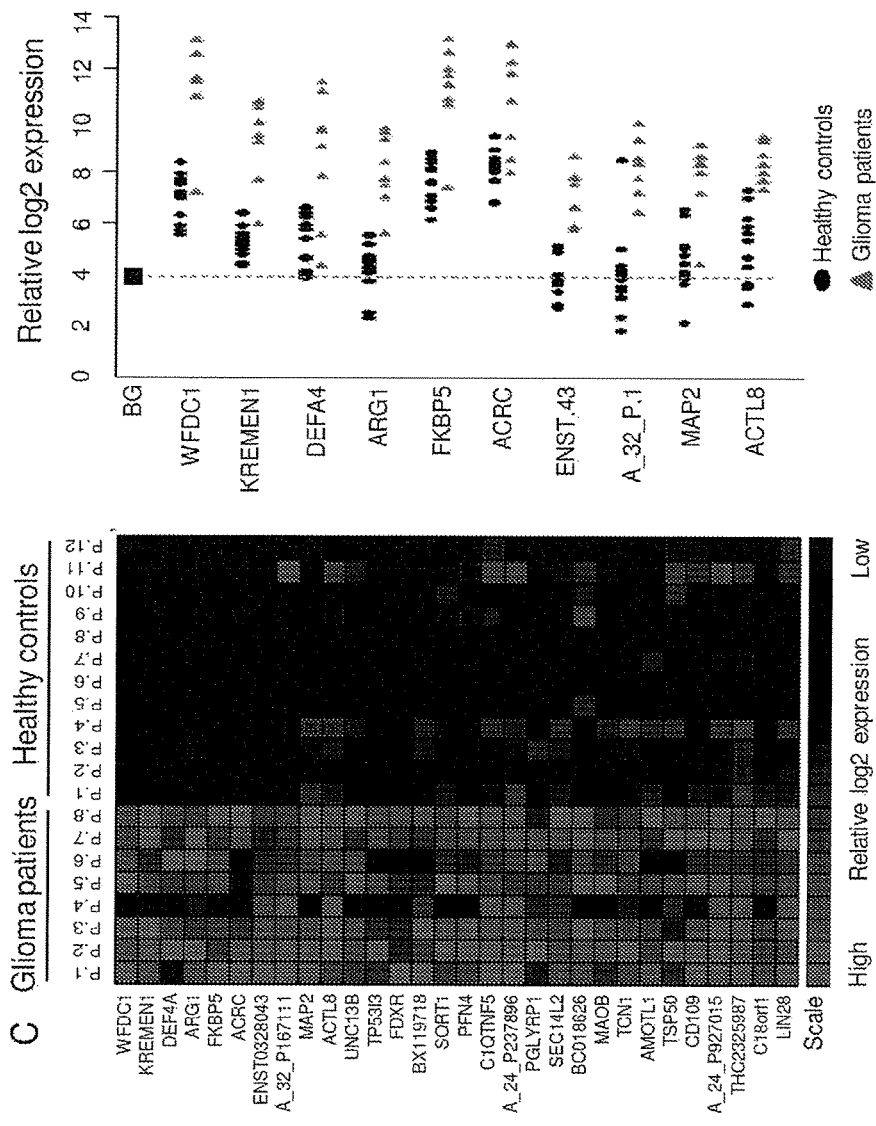

Apart from detecting gene mutations associated with cancer or other diseases, the present inventors also found that gene expression arrays could be used to classify a thrombocytes nucleic acid sample as being that of a subject suffering from a specific type of (solid tumour) cancer or other disease. It was established that mRNA expression profiles obtained with nucleic acids extracted from platelets isolated from healthy control subjects or extracted from platelets isolated from glioma patients differed specifically. Distinct mRNA expression profiles were obtained and a minimal glioma biomarker signature could be detected, as shown for the Top-30 hits in FIG. 3C. The distinct profile as shown in FIG. 3C comprises a significant increase in the expression of the following genes: WFDC1, Kremenl, DEF4A, ARG1, FKBP5, ACRC, ENST0328043, A_32_P167111, MAP2, ECTL8, UNC13B, TP5313, FDXR, BX119718, SORT1, PFN4, C1QTNF5, A_24_P237896, PGLYRP1, SEC14L2, BC018626, MAOB, TCN1, AMOTL1, TSP50, A_24_P927015, THC2325987, C18orf1, and LIN28 (some of these gene names are referred to with reference to the Microarray Accession number, e.g. the oligonucleotide probe of the Agilent Chip). It will be understood that this profile is not limitative to the scope of the present invention, since the skilled person is well aware how to obtain other suitable gene expression profiles using the methods of the present invention for other cancers, and for other diseases in general.

The present inventors have now found that blood platelets contain cancer markers and disease markers in the form of tumor-derived or tumor-associated or disease-derived nucleic acids or nucleic acid expression profiles and that these platelets may serve as a diagnostic platform for the molecular profiling of cancer and other diseases as identified herein. This is highly useful in the context of personalized medicine.

The present invention provides a novel and easy-to-use method to isolate circulating disease-derived material (e.g. disease markers as used herein) for genetic analysis. The present inventors isolated tumor-derived RNA from circulating thrombocytes, yielding pure RNA and thereby providing an easy way to extract high quality RNA from low amounts of blood. Thrombocyte nucleic acid (NA) isolation and subsequent analysis presents a marked increase in the diagnostic sensitivity of circulating NA in blood.

The present inventors found that in diseased patients circulating thrombocytes contain significant amounts of disease-derived RNA and/or DNA. This disease-derived RNAs and/or DNAs presents unique genetic information about the disease, which may be used to determine disease type, extent of disease and possibly the susceptibility of the disease to therapeutic treatment. In a preferred embodiment of a method or embodiment of the invention said disease is not cancer.

In another preferred embodiment of a method or embodiment of the invention said disease is not a vascular disease.

In another preferred embodiment of a method or embodiment of the invention said disease is not systemic lupus erythematosus.

In another preferred embodiment of a method or embodiment of the invention said disease is not sickle cell disease.

In another preferred embodiment of a method or embodiment of the invention said disease is not Alzheimer's disease.

In another preferred embodiment of a method or embodiment of the invention said disease is not a disease associated with pathological megakaryocyte function.

In another preferred embodiment of a method or embodiment of the invention said disease is not a disease associated with pathological platelet function.

The above-referenced preferred embodiments wherein certain diseases are disclaimed can be combined in any manner in aspects of this invention.

In a preferred embodiment of the method of the invention and embodiments thereof the disease is not a disease selected from the group comprising cancer, cardiovascular disease, systemic lupus erythematosus, sickle cell disease, Alzheimer's disease, diseases associated with pathological platelet function, and/or diseases associated with pathological megakaryocyte function.

Diseases involving abnormal platelet function may comprise post-transfusion purpura (PTP), post transfusion platelet refractoriness (PTPR), nenotal alloimmune thrombocytopenia (NATP), thrombocytopenia, and/or orthrombocythaemia.

In another preferred embodiment of a method or embodiment of the invention said disease-derived nucleic acid does not originate from a megakaryocyte. It is expressly indicated that the nucleic acid subject of this invention is taken up or accumulated by the thrombocyte from the extracellular (blood plasma) environment, and not megakaryocyte-lineage derived. The thrombocyte RNA and/or DNA can be analyzed for the presence of specific disease-derived RNAs and/or DNAs, as demonstrated herein for the EGFRvIII mutant RNA derived from glioma tumours.

The present invention describes a method of finding specific nucleic acid transcripts derived from nucleated cells of disease origin within anucleated blood cells such as thrombocytes extracted from blood. This approach is robust and easy. This is attributed to the rapid and straight forward extraction procedures and the quality of the extracted NA. Within the clinical setting, thrombocytes extraction (from blood samples) is already implemented in general biological sample collection and therefore it is foreseen that the implementation into the clinic is relatively easy.

The present invention provides a general method for analysing blood of a subject for the presence of a disease-derived nucleic acid and a method of diagnosing disease in a subject using said general method. When reference is herein made to a method of the invention, both embodiments are referred to.

A method of the invention can be performed on any suitable body sample comprising anucleated blood cells, such as for instance a tissue sample comprising blood, but preferably said sample is whole blood.

A blood sample of a subject can be obtained by any standard method, for instance by venous extraction.

The amount of blood needed is not particularly limited. Depending on the methods employed, the skilled person will be capable of establishing the amount of sample required to perform the various steps of the method of the present invention and obtain sufficient NA for genetic analysis. Generally, such amounts will comprise a volume ranging from 0.01 µl to 100 ml.

The body sample may be analyzed immediately following collection of the sample. Alternatively, analysis according to the method of the present invention can be performed on a stored body sample or on a stored fraction of anucleated blood cells thereof, preferably thrombocytes. The body sample for testing, or the fraction of anucleated blood cells thereof, can be preserved using methods and apparatuses known in the art. In a collected anucleated blood cell fraction, the thrombocytes are preferably maintenance in inactivated state (i.e. in non-activated state). In that way, the cellular integrity and the disease-derived nucleic acids are best preserved.

In case the fraction of anucleated blood cells is a thrombocyte fraction, this platelet isolated fraction does preferably not include platelet poor plasma or platelet rich plasma (PRP). Further isolation of the platelets is preferred for optimal resolution.

The body sample may suitably be processed otherwise, for instance, it may be purified, or digested, or specific compounds may be extracted therefrom. Depending upon the method of characterizing the NA present in the anucleated blood cells in said sample, which method preferably involves RT-PCR, the anucleated blood cells may be extracted from the sample by methods known to the skilled person and be transferred to any suitable medium for extraction of the NA therefrom should the analysis method so require. The recipient subject's body sample may be treated to remove abundant nucleic acid degrading enzymes (like RNases, DNases) therefrom, in order to prevent early destruction of the nucleic acids.

Thrombocyte extraction from the body sample of the subject may involve any available method. In transfusion medicine, thrombocytes are often collected by apheresis, a medical technology in which the blood of a donor or patient is passed through an apparatus that separates out one particular constituent and returns the remainder to the circulation. The separation of individual blood components is done with a specialized centrifuge. Plateletpheresis (also called thrombopheresis or thrombocytapheresis) is the apheresis process of collecting thrombocytes. Modern automatic plateletpheresis allows blood donors to give a portion of their thrombocytes, while keeping their red blood cells and at least a portion of blood plasma. Although it is possible to provide the body sample comprising thrombocytes as envisioned herein by apheresis, it is often easier to collect whole blood and isolate the thrombocyte fraction therefrom by centrifugation. Generally, in such a protocol, the thrombocytes are first separated from the other blood cells by a centrifugation step of about 120×g for about 20 minutes at room temperature to obtain a platelet rich plasma (PRP) fraction. The thrombocytes are then washed (for instance in PBS-EDTA) to remove plasma proteins and enrich for thrombocytes. Wash steps are generally carried out at 850-1000×g for about 10 min at room temperature. Further enrichments can be carried out to yield more pure thrombocyte fractions.

Platelet isolation generally involves blood sample collection in Vacutainer tubes containing anticoagulant citrate dextrose (e.g. 36 ml citric acid, 5 mmol/l KCl, 90 mmol/l NaCl, 5 mmol/l glucose, 10 mmol/l EDTA pH 6.8). A suitable protocol for platelet isolation is described in Ferretti et al. (J Clin Endocrinol Metab 2002; 87:2180-2184). This method involves a preliminary centrifugation step (1,300 rpm per 10 min) to obtain platelet-rich plasma (PRP). Platelets are then washed three times in an anti-aggregation buffer (Tris-HCl 10 mmol/l; NaCl 150 mmol/l; EDTA 1 mmol/l; glucose 5 mmol/l; pH 7.4) and centrifuged as above, to avoid any contamination with plasma proteins and to remove any residual erythrocytes. A final centrifugation at 4,000 rpm for 20 min may then be performed to isolate platelets. The platelet pellet may be washed (e.g. in phosphate buffered saline For quantitative determination of disease marker levels, the protein concentration of platelet membranes may be used as internal reference. Such protein concentrations may be determined by the method of Bradford (Anal Biochem 1976; 72:248-254), using serum albumin as standard.

Following the provision of the body sample of the subject, and the extraction therefrom of the anucleated blood cells, the anucleated blood cells of the subject are screened for the presence of disease-specific nucleic acids. If disease-specific nucleic acids are encountered in the anucleated blood cells of the subject, or if disease-specific nucleic acids are encountered in the anucleated blood cells of the subject at a higher level than in the anucleated blood cells in an unaffected blood sample of a control subject, which disease-specific nucleic acids are considered to originate from a diseased cell or tissue residing in the subject, said subject is diagnosed with disease as defined herein.

Disease-specific nucleic acids (RNA and/or DNA disease markers) are defined as originating from disease cells that contain mutations or no mutations in the nucleic acid sequences that are associated with or specific to the disease, and also include disease-derived anucleated blood cells nucleic acids which are up- or down-regulated as compared to nucleic acids in anucleated blood cells from healthy donors. Hence, the terms "disease-specific nucleic acids" and "disease-derived nucleic acids" are used interchangeable herein. It will be appreciated that non-mutated genes can be identified and used for disease diagnostics. If certain genes are overexpressed in certain diseases, these nucleic acids may be transferred to anucleated blood cells. However, if these nucleic acids are already present in anucleated blood cells of healthy subjects one can expect an increase in the number of nucleic acid copies in anucleated blood cells of such diseased patients. Hence, quantification of the copy number of certain genes (by quantitative PCR or microarrays e.g.) in anucleated blood cells may be beneficial in certain embodiments of aspects of this invention for detecting the presence of a diseases overexpressing such genes. Preferably the disease marker or disease-specific nucleic acids are not derived from a megakaryocyte. In a preferred embodiment of the present invention and embodiments thereof the disease marker or disease specific nucleic acid is not a mutation at position 12027 in mitochondrial DNA. In a preferred embodiment of the present invention and embodiments thereof the disease marker or disease specific nucleic acid is not a mutation at position 11778 in mitochondrial DNA. In a preferred embodiment of the present invention and embodiments thereof the disease marker or disease specific nucleic acid is not a mutation in the CD109 gene. In a preferred embodiment of the present invention and embodiments thereof the disease marker or disease specific nucleic acid is not a mutation at position 2108 and/or position 954 of the coding region of the CD109 gene. Any of the above disclaimed embodiments may be disclaimed in any combination in aspects herein.

A further step in a method of the invention is the provision of an anucleated blood cells-extracted nucleic acid fraction. Such a nucleic acid fraction is subsequently used for the detection of a disease marker therein. An anucleated blood cells-extracted nucleic acid fraction may be obtained by any NA extraction method available. Usually RNA extraction is performed by using chaotropic reagents. The first step in isolating total RNA from cells or tissue is to break open the cells under denaturing conditions. In 1979, Chirgwin et al.

(Biochemistry, 18[24]:5294-9, 1979) devised a method for the efficient isolation of total RNA by homogenization in a 4 M solution of the potent protein denaturant guanidinium thiocyanate with 0.1 M 2-mercaptoethanol to break protein disulfide bonds. RNA was then isolated by ethanol extraction or by ultracentrifugation through cesium chloride. In 1987 Chomczynski and Sacchi (Analytical Biochemistry, 162[1]:156-9, 1987) modified this method to devise a rapid single-step extraction procedure using a mixture of guanidinium thiocyanate and phenol-chloroform, a method especially useful for processing large numbers of samples or for isolation of RNA from small quantities of cells or tissue. Any commercial kit can also be used for the extraction of RNA, non-limiting examples thereof include Ambion's RNAqueous™ system, Bio101's RNaid Plus kit, Bioline Ltd.'s RNAce kits, CLONTECH's NucleoSpin® RNA II and NucleoTrap mRNA kits, Invitrogen Corp.'s S.N.A.P. Total RNA Isolation Kit and QIAGEN's RNeasy kits.

The detection of a disease-derived nucleic acid in the extracted nucleic acid sample may occur by any genetic analysis technique available that is suitable for the detection of nucleic acid sequence mutations or expression profiles in nucleic acids that are specific for the disease. Usually, such sequence mutations can be easily detected by selective nucleic acid hybridization, involving the formation of a duplex nucleic acid structure formed by selective hybridization with each other of two single-stranded nucleic acid sequences. Selective hybridization includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

Alternatively, detection of a disease-derived nucleic acid may occur through sequencing technologies such as DNA and RNA sequencing.

When detecting sequence mutations in RNA, or expression profiles of RNA, it is preferred that the RNA is transcribed into cDNA prior to the detection of sequence mutations therein or quantitation of the amount expressed.

RNA can be reverse transcribed into cDNA using RNA-dependent DNA polymerases such as, for example, reverse transcriptases from viruses, retrotransposons, bacteria, etc. These can have RNase H activity, or reverse transcriptases can be used that are so mutated that the RNase H activity of the reverse transcriptase was restricted or is not present (e.g. MMLV-RT RNase H⁻). RNA-dependent DNA synthesis (reverse transcription) can also be carried by enzymes that show altered nucleic acid dependency through mutation or modified reaction conditions and thus obtain the function of the RNA-dependent DNA polymerase. Commercial kits are available to reverse transcribe RNA into cDNA.

Once the RNA is reverse transcribed into cDNA, the DNA sequence can be analysed for the presence of cancer-specific mutations or expression profiles can be determined using for instance selective nucleic acid hybridization as described above. Such techniques are well known in the art and may comprise selective amplification using amplification primers that are specific for the mutation to be detected or selective hybridization to nucleic acid arrays using mRNA-specific probes. Alternatively, general primers can be used to amplify the DNA comprising the suspected mutation and the mutation can than be detected in the amplicon by selective nucleic acid hybridization using probes that are specific for the mutation. Expression profiles are generally obtained using methods of quantitative hybridization well described in the art, an illustration of which is described in the Examples.

Methods of the invention can in principle be performed by using any nucleic acid amplification method, such as the Polymerase Chain Reaction (PCR; Mullis 1987, U.S. Pat. Nos. 4,683,195, 4,683,202, en 4,800,159) or by using amplification reactions such as Ligase Chain Reaction (LCR; Barany 1991, Proc. Natl. Acad. Sci. USA 88:189-193; EP Appl. No., 320,308), Self-Sustained Sequence Replication (3SR; Guatelli et al., 1990, Proc. Natl. Acad. Sci. USA 87:1874-1878), Strand Displacement Amplification (SDA; U.S. Pat. No. 5,270,184, en U.S. Pat. No. 5,455,166), Transcriptional Amplification System (TAS; Kwoh et al., Proc. Natl. Acad. Sci. USA 86:1173-1177), Q-Beta Replicase (Lizardi et al., 1988, Bio/Technology 6:1197), Rolling Circle Amplification (RCA; U.S. Pat. No. 5,871,921), Nucleic Acid Sequence Based Amplification (NASBA), Cleavase Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of DNA.

In order to amplify DNA with a small number of mismatches to one or more of the amplification primers, an amplification reaction may be performed under conditions of reduced stringency (e.g. a PCR amplification using an annealing temperature of 38° C., or the presence of 3.5 mM $MgCl_2$). The person skilled in the art will be able to select conditions of suitable stringency.

The primers herein are selected to be "substantially" complementary (i.e. at least 65%, more preferably at least 80% perfectly complementary) to their target regions present on the different strands of each specific sequence to be amplified. It is possible to use primer sequences containing e.g. inositol residues or ambiguous bases or even primers that contain one or more mismatches when compared to the target sequence. In general, sequences that exhibit at least 65%, more preferably at least 80% homology with the target DNA oligonucleotide sequences, are considered suitable for use in a method of the present invention. Sequence mismatches are also not critical when using low stringency hybridization conditions.

The detection of the amplification products can in principle be accomplished by any suitable method known in the art. The detection fragments may be directly stained or labelled with radioactive labels, antibodies, luminescent dyes, fluorescent dyes, or enzyme reagents. Direct DNA stains include for example intercalating dyes such as acridine orange, ethidium bromide, ethidium monoazide or Hoechst dyes.

Alternatively, the DNA fragments may be detected by incorporation of labelled dNTP bases into the synthesized DNA fragments. Detection labels which may be associated with nucleotide bases include e.g. fluorescein, cyanine dye or BrdUrd.

When using a probe-based detection system, a suitable detection procedure for use in the present invention may for example comprise an enzyme immunoassay (EIA) format (Jacobs et al., 1997, J. Clin. Microbiol. 35, 791795). For performing a detection by manner of the EIA procedure, either the forward or the reverse primer used in the amplification reaction may comprise a capturing group, such as a biotin group for immobilization of target DNA PCR amplicons on e.g. a streptavidin coated microtiter plate wells for subsequent EIA detection of target DNA amplicons (see below). The skilled person will understand that other groups for immobilization of target DNA PCR amplicons in an EIA format may be employed.

Probes useful for the detection of the target DNA as disclosed herein preferably bind only to at least a part of the DNA sequence region as amplified by the DNA amplification procedure. Those of skill in the art can prepare suitable probes for detection based on the nucleotide sequence of the target DNA without undue experimentation as set out herein. Also the complementary sequences of the target DNA may suitably be used as detection probes in a method of the invention, provided that such a complementary strand is amplified in the amplification reaction employed.

Suitable detection procedures for use herein may for example comprise immobilization of the amplicons and probing the DNA sequences thereof by e.g. southern blotting. Other formats may comprise an EIA format as described above. To facilitate the detection of binding, the specific amplicon detection probes may comprise a label moiety such as a fluorophore, a chromophore, an enzyme or a radio-label, so as to facilitate monitoring of binding of the probes to the reaction product of the amplification reaction. Such labels are well-known to those skilled in the art and include, for example, fluorescein isothiocyanate (FITC), β-galactosidase, horseradish peroxidase, streptavidin, biotin, digoxigenin, $^{35}S$ or $^{125}I$. Other examples will be apparent to those skilled in the art.

Detection may also be performed by a so called reverse line blot (RLB) assay, such as for instance described by Van den Brule et al. (2002, J. Clin. Microbiol. 40, 779-787). For this purpose RLB probes are preferably synthesized with a 5' amino group for subsequent immobilization on e.g. carboxylcoated nylon membranes. The advantage of an RLB format is the ease of the system and its speed, thus allowing for high throughput sample processing.

The use of nucleic acid probes for the detection of DNA fragments is well known in the art. Mostly these procedures comprise the hybridization of the target DNA with the probe followed by post-hybridization washings. Specificity is typically the function of post-hybridization washes, the critical factors being the ionic strength and temperature of the final wash solution. For DNA-DNA hybrids, the $T_m$ (the thermal melting point, i.e. the temperature under defined ionic strength and pH at which 50% of a complementary target sequence hybridizes to a perfectly matched probe) can be approximated from the equation of Meinkoth and Wahl (Anal. Biochem., 138: 267-284 (1984)): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is reduced by about 1° C. for each 1% of mismatching; thus, the hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than $T_m$ Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology-Hybridization with Nucleic Acid Probes, Part I, Chapter 2 "Overview of principles of hybridization and the strategy of nucleic acid probe assays", Elsevier. New York (1993); and Current Protocols in Molecular Biology, Chapter 2, Ausubel, et al., Eds., Greene Publishing and Wiley-Interscience, New York (1995).

Detection probes are preferably selected to be "substantially" complementary to one of the strands of the double stranded DNA amplicons generated by an amplification reaction in a method of the invention. Preferably the probes are substantially complementary to the immobilizable (e.g. biotin labelled) antisense strands of the amplicons generated from the target DNA.

It is allowable for detection probes to contain one or more mismatches to their target sequence. In general, sequences that exhibit at least 65%, more preferably at least 80% homology with the target DNA oligonucleotide sequences are considered suitable for use in a method of the present invention.

The step of analysing the anucleated blood cell-extracted nucleic acid fraction for the presence of a disease marker can thus be performed by standard nucleic acid analysis techniques. The step of determining whether there is an alteration in the level of said nucleic acid marker in said nucleic acid fraction with respect to an unaffected blood sample will involve (semi-) quantitative measurements of the amount of disease marker in the anucleated blood cells. A much preferred protocol for the detection of disease-specific markers in the nucleic acids isolated from anucleated blood cells is therefore quantitative reverse-transcription PCR (qRT-PCR) (Freeman et al., BioTechniques 26:112-125 (1999)).

An "unaffected blood sample" as referred to above refers to the level of the disease marker in anucleated blood cells of a healthy control subject or from the same subject prior to the onset of the disease. Since anucleated blood cell characteristics and quantities of anucleated blood cell components depend on, amongst other things, species and age, it is preferable that the non-diseased control anucleated blood cells come from a subject of the same species, age and from the same sub-population (e.g. smoker/nonsmoker). Alternatively, control data may be taken from databases and literature. It will be appreciated that the control sample may also be taken from the diseased subject at a particular time-point, in order to analyze the progression of the disease.

Disease markers include cancer/specific mutations and cancer-specific mutations may include a wide variety of mutations known to be associated with cancer. A non-limiting list of examples of mutations for various cancers is provided at http://www.sanger.ac.uk/genetics/CGP/Census/ and in the Tables herein.

The invention further provides a kit for diagnosing disease in a subject, the kit comprising a packaging material which comprises at least one agent for specifically determining a level and/or activity of at least one nucleic acid mutant and/or nucleic acid profile in an anucleated blood cell sample of the subject. As used herein, the term "diagnosing" refers to determining the presence of a disease, classifying a disease, determining a severity of disease (grade or stage), monitoring disease progression, forecasting an outcome of the disease and/or prospects of recovery.

It will be appreciated that the tools necessary for detecting the disease-derived nucleic acid may be provided as a kit, such as an FDA-approved kit, which may contain one or more unit dosage form containing the active ingredient for detection of the disease-derived nucleic acid in anucleated blood cells by a method of the present invention.

Alternatively, the kit may comprise means for collecting the sample and specific amplification and/or detection primers packaged separately.

The kit may be accompanied by instructions for performing a method of the present invention.

For example, the kit may be comprised in a device such as a dipstick or a cartridge, (optionally comprised in a housing) to which a blood sample or an isolated and/or amplified anucleated blood cell nucleic acid sample may be applied and which detects a disease-derived or disease-specific nucleic acid or nucleic acid profile in said sample. The device may comprise any agent capable of specifically detecting the disease-derived nucleic acid. For example, the device may comprise one or a combination of immobilized mutation-specific hybridization probes that bind the disease-derived nucleic acid and an indicator for detecting binding. In an embodiment of this invention, supports are provided in the device to which the hybridization probes are removably or fixedly attached.

According to one embodiment, the device may be a lateral flow device comprising inlet means for flowing a blood sample or an isolated and/or amplified anucleated blood cell nucleic acid sample into contact with the agents capable of detecting the disease-derived nucleic acid. The test device can also include a flow control means for assuring that the test is properly operating. Such flow control means can include control nucleic acids bound to a support which capture detection probes added to the sample as a means of confirming proper flow of sample fluid through the test device. Alternatively, the flow control means can include capture probes in the control region which capture control nucleic acids naturally present in said sample or added thereto as control, again indicating that proper flow is taking place within the device.

In another aspect, the present invention provides the use of device of the present invention for diagnosing disease in a subject using any one of the methods described herein above. Very suitable devices for use in diagnosing disease in a subject using any one of the methods described herein above include Platelet RNA chips such as for instance described in Nagalla & Bray (2010) Blood 115 (1): 2-3 and Gnatenko et al. Blood 115 (1): 7-14.

The invention will now be exemplified by means of the following non-limiting examples.

EXAMPLES

Example 1

Thrombocytes were isolated from blood samples of 4 glioblastoma patients and 4 healthy donors by centrifugation steps. The thrombocytes were then subjected to RNA extraction using Trizol RNA isolation. The purified thrombocytic RNA samples were then converted to cDNA and analyzed by Agilent 4×44K expression microarrays using standard microarray protocols. This allowed the profiling of the mRNAs in the different thrombocyte preparations.

About 8500 RNA transcripts could not be detected by expression microarrays in platelets from healthy donors. These transcripts were present at levels below the detection limit of the Agilent 4×44K chip in thrombocytes from healthy donors. Hence, such RNAs may all be potential biomarkers for cancer diagnostics. Of the RNAs not detected by expression microarrays in thrombocytes from healthy donors, a substantial set of RNAs was detected in thrombocytes from glioblastoma patients. Table 1 summarizes unique thrombocytic RNA transcripts detected in thrombocytes from glioblastoma patients but not in thrombocytes from healthy donors by expression microarrays. Unique RNA transcripts detected in 4/4 patient samples (Table 1A) or in 3/4 patient samples (Table 1B), but not in any of the four control samples are summarized in Table 1.

TABLE 1

Unique thrombocytic RNA transcripts detected in thrombocytes from glioblastoma patients but not in thrombocytes from healthy donors by expression microarrays.

1A. Transcripts detected in thrombocytes in four out of four patient samples, but not detected in thrombocytes from control samples.

| | | | | |
|---|---|---|---|---|
| A_23_P207233 | A_23_P47546 | A_24_P452024 | A_24_P642240 | A_24_P654255 |
| A_24_P712193 | A_24_P816073 | A_32_P142521 | A_32_P167111 | A_32_P35839 |
| A_32_P59532 | AA594975 | AF035790 | AF119839 | AF130062 |
| AI138440 | AK098562 | ASPM | AW269819 | BC002534 |
| BC024745 | BC047055 | BHMT | BM683433 | BX118161 |
| C10orf10 | C9orf138 | CCL16 | CENPQ | CLN5 |
| CLTCL1 | COCH | CPA6 | CUTL2 | DKFZp547H025 |
| DLSTP | DNAJC5B | ENST00000303697 | ENST00000315208 | ENST00000382726 |
| FILIP1 | GAL | GPR149 | GTSE1 | HAS3 |
| HFE | HOXB6 | HOXD11 | IGF1 | IL21 |
| LDLR | LOC221710 | LOC388160 | LOC641999 | LRRC2 |
| LRRC4 | MGC16291 | MPDZ | MYCL1 | NPR3 |
| OLAH | OR2H1 | PLK4 | PNMA2 | ROBO4 |
| SEPT10 | SLC14A1 | SP2 | SPANXB2 | TAF5L |
| TCEAL7 | THC2279825 | THC2334717 | THC2340924 | THC2412206 |
| TIMP4 | TMPRSS3 | TNFAIP6 | TNK1 | ZNF596 |

1B. Transcripts detected in thrombocytes in three out of four patient samples, but not detected in thrombocytes from control samples.

| | | | | |
|---|---|---|---|---|
| A_23_P72252 | A_24_P195400 | A_24_P195621 | KRT8P23 | A_24_P246777 |
| A_24_P315255 | A_24_P647965 | A_24_P669822 | A_24_P752208 | A_24_P790361 |
| A_24_P834066 | A_24_P915245 | A_24_P928453 | A_24_P929126 | A_24_P931713 |

TABLE 1-continued

Unique thrombocytic RNA transcripts detected in thrombocytes from glioblastoma patients but not in thrombocytes from healthy donors by expression microarrays.

| | | | | |
|---|---|---|---|---|
| A_24_P933278 | A_24_P934497 | A_24_P935492 | A_32_P119949 | A_32_P136427 |
| A_32_P15328 | A_32_P182135 | A_32_P69993 | A_32_P743731 | A_32_P75311 |
| A_32_P92274 | AA420988 | AA669267 | AA843546 | AA890136 |
| AA918648 | ABCA10 | ABCB9 | ACADL | ACE |
| ADAM32 | AF119848 | AF136408 | AF217973 | AF263545 |
| AF315716 | AF401032 | AI291464 | AI335947 | AI885257 |
| AK021897 | AK057725 | AK057935 | AK074369 | AK091028 |
| AK096102 | AK096991 | AK130038 | AL133089 | ALDH5A1 |
| ANKRD40 | APOA1 | APOA1 | APOD | AW385956 |
| AY358234 | BC017851 | BC037882 | BC038740 | BC041899 |
| BC37295_3 | BCL2L11 | BF376089 | BF435769 | BF509481 |
| BF826743 | BHMT2 | BHMT2 | BM476468 | BM681332 |
| BPI | BQ028381 | BX091616 | BX647685 | C15orf37 |
| C17orf53 | C18orf56 | C20orf117 | C3orf23 | C4orf6 |
| C4orf7 | C6orf10 | C6orf52 | C9orf39 | CART1 |
| CC2D1A | CCL7 | CDC2 | CES4 | CF527929 |
| CITED4 | CLDN4 | CNTN2 | COL1A1 | COL5A2 |
| COL6A1 | COX11 | CPLX2 | CPNE6 | CRB1 |
| DB380193 | DENND1A | DPPA5 | DST | EFEMP1 |
| EGFR | ENST00000254271 | ENST00000258873 | ENST00000272235 | ENST00000295989 |
| ENST00000299308 | ENST00000300996 | ENST00000315293 | ENST00000335534 | ENST00000354261 |
| ENST00000354417 | ENST00000355077 | ENST00000355247 | ENST00000356104 | ENST00000369615 |
| ENST00000374334 | ENST00000374458 | ENST00000375587 | ENST00000381050 | ENTPD8 |
| EPS8L3 | ERVWE1 | ESX1 | F8 | FAM104B |
| FAM62C | FAM71B | FAM9C | FBXW10 | FCRL4 |
| FGFR1 | FLJ25715 | FLJ32312 | FLJ37543 | FLJ39582 |
| FLJ39779 | FNDC5 | FRG2 | FSIP2 | FTCD |
| GAPDHS | GAS2L2 | GAS8 | GCKR | GLRA1 |
| GPR143 | GPR98 | GUCA1C | HILS1 | HLA-DRB6 |
| HOXD3 | HR44 | IGF1 | IGF1 | IGSF4 |
| INHBA | ITGAV | JPH1 | KIAA0492 | KIAA1661 |
| KIF20A | KLHL9 | KREMEN1 | LCE3B | LENEP |
| LIFR | LOC222171 | LOC339524 | LOC348021 | LOC388503 |
| LOC390211 | LOC440295 | LOC642730 | LOC643100 | LOC643125 |
| LOC648556 | LOC92270 | M31157 | MGC39584 | MGC43122 |
| MRAP | MSTO1 | MYLC2PL | MYO7A | NDST3 |
| NF2 | NNMT | NR1H4 | NTN1 | NTRK3 |
| NTS | NXPH3 | ODAM | OPCML | OR8H1 |
| PALM2-AKAP2 | PAX9 | PCNXL2 | PHC2 | PKNOX1 |
| PLAC1 | POTE2 | PPCDC | PPFIBP1 | PPP1R14C |
| RBMY2EP | RCBTB1 | RHOD | RRAGB | RSHL1 |
| RSPO1 | S72478 | SAA4 | SASS6 | SDK1 |
| SLC22A9 | SLC26A9 | SLCO1A2 | SNAP25 | SP5 |
| SPBC25 | STEAP1 | SUFU | SUNC1 | SYCE1 |
| SYT12 | TAS2R38 | TAS2R4 | TBC1D3 | TBC1D8B |
| TCEB3C | TEK | THC2269604 | THC2269920 | THC2276996 |
| THC2279230 | THC2281591 | THC2281747 | THC2286878 | THC2286962 |
| THC2289112 | THC2296760 | THC2316481 | THC2316929 | THC2339079 |
| THC2339904 | THC2347643 | THC2369034 | THC2374304 | THC2374505 |
| THC2380237 | THC2385918 | THC2407039 | THC2444579 | THC2454812 |
| THRSP | TM4SF20 | TNFRSF13B | TREH | TRPA1 |
| TRPC7 | TSC22D2 | TSHZ2 | TTTY6 | UGT8 |
| UNC13B | USP2 | USP6 | VLDLR | WWTR1 |
| X87895 | ZNF28 | ZNF57 | | |

TABLE 2

Cancer-specific mutations for various cancers.

| Symbol | GeneID | Chr Band | Tumour Types (Somatic Mutations) | Cancer Syndrome |
|---|---|---|---|---|
| ABL1 | 25 | 9q34.1 | CML, ALL, T-ALL | |
| ABL2 | 27 | 1q24-q25 | AML | |
| ACSL3 | 2181 | 2q36 | prostate | |
| AF15Q14 | 57082 | 15q14 | AML | |
| AF1Q | 10962 | 1q21 | ALL | |
| AF3p21 | 51517 | 3p21 | ALL | |
| AF5q31 | 27125 | 5q31 | ALL | |
| AKAP9 | 10142 | 7q21-q22 | papillary thyroid | |
| AKT1 | 207 | 14q32.32 | breast, colorectal, ovarian, NSCLC | |
| AKT2 | 208 | 19q13.1-q13.2 | ovarian, pancreatic | |
| ALK | 238 | 2p23 | ALCL, NSCLC, Neuroblastoma | Familial neuroblastoma |
| ALO17 | 57714 | 17q25.3 | ALCL | |

TABLE 2-continued

Cancer-specific mutations for various cancers.

| Symbol | GeneID | Chr Band | Tumour Types (Somatic Mutations) | Cancer Syndrome |
|---|---|---|---|---|
| APC | 324 | 5q21 | colorectal, pancreatic, desmoid, hepatoblastoma, glioma, other CNS | Adenomatous polyposis coli; Turcot syndrome |
| ARHGEF12 | 23365 | 11q23.3 | AML | |
| ARHH | 399 | 4p13 | NHL | |
| ARNT | 405 | 1q21 | AML | |
| ASPSCR1 | 79058 | 17q25 | alveolar soft part sarcoma | |
| ASXL1 | 171023 | 20q11.1 | MDS, CMML | |
| ATF1 | 466 | 12q13 | malignant melanoma of soft parts, angiomatoid fibrous histiocytoma | |
| ATIC | 471 | 2q35 | ALCL | |
| ATM | 472 | 11q22.3 | T-PLL, leukemia, lymphoma, medulloblastoma, glioma | Ataxia-telangiectasia |
| BCL10 | 8915 | 1p22 | MALT | |
| BCL11A | 53335 | 2p13 | B-CLL | |
| BCL11B | 64919 | 14q32.1 | T-ALL | |
| BCL2 | 596 | 18q21.3 | NHL, CLL | |
| BCL3 | 602 | 19q13 | CLL | |
| BCL5 | 603 | 17q22 | CLL | |
| BCL6 | 604 | 3q27 | NHL, CLL | |
| BCL7A | 605 | 12q24.1 | BNHL | |
| BCL9 | 607 | 1q21 | B-ALL | |
| BCR | 613 | 22q11.21 | CML, ALL, AML | |
| BHD | 201163 | 17p11.2 | renal, fibrofolliculomas, trichodiscomas | Birt-Hogg-Dube syndrome |
| BIRC3 | 330 | 11q22-q23 | MALT | |
| BLM | 641 | 15q26.1 | leukemia, lymphoma, skin squamous cell, other cancers | Bloom Syndrome |
| BMPR1A | 657 | 10q22.3 | gastrointestinal polyps | Juvenile polyposis |
| BRAF | 673 | 7q34 | melanoma, colorectal, papillary thyroid, borderline ov, Non small-cell lung cancer (NSCLC), cholangiocarcinoma, pilocytic astrocytoma | |
| BRCA1 | 672 | 17q21 | ovarian, breast, | Hereditary breast/ovarian cancer |
| BRCA2 | 675 | 13q12 | breast, ovarian, pancreatic, leukemia (FANCB, FANCD1) | Hereditary breast/ovarian cancer |
| BRD3 | 8019 | 9q34 | lethal midline carcinoma of young people | |
| BRD4 | 23476 | 19p13.1 | lethal midline carcinoma of young people | |
| BRIP1 | 83990 | 17q22 | AML, leukemia, breast | Fanconi anaemia J, breast cancer susceptiblity |
| BTG1 | 694 | 12q22 | BCLL | |
| BUB1B | 701 | 15q15 | rhabdomyosarcoma | Mosaic variegated aneuploidy |
| C12orf9 | 93669 | 12q14.3 | lipoma | |
| C15orf21 | 283651 | 15q21.1 | prostate | |
| CANT1 | 124583 | 17q25 | prostate | |
| CARD11 | 84433 | 7p22 | DLBL | |
| CARS | 833 | 11p15.5 | ALCL | |
| CBFA2T1 | 862 | 8q22 | AML | |
| CBFA2T3 | 863 | 16q24 | AML | |
| CBFB | 865 | 16q22 | AML | |
| CBL | 867 | 11q23.3 | AML, JMML, MDS | |
| CBLB | 868 | 3q13.11 | AML | |
| CBLC | 23624 | 19q13.2 | AML | |
| CCND1 | 595 | 11q13 | CLL, B-ALL, breast | |
| CCND2 | 894 | 12p13 | NHL, CLL | |
| CCND3 | 896 | 6p21 | MM | |
| CD74 | 972 | 5q32 | NSCLC | |
| CD79A | 973 | 19q13.2 | DLBCL | |
| CD79B | 974 | 17q23 | DLBCL | |
| CDH1 | 999 | 16q22.1 | lobular breast, gastric | Familial gastric carcinoma |
| CDH11 | 1009 | 16q22.1 | aneurysmal bone cysts | |
| CDK4 | 1019 | 12q14 | melanoma | Familial malignant melanoma |
| CDK6 | 1021 | 7q21-q22 | ALL | |
| CDKN2A-p16(INK4a) | 1029 | 9p21 | melanoma, multiple other tumour types, pancreatic | Familial malignant melanoma |
| CDKN2A-p14ARF | 1029 | 9p21 | melanoma, multiple other tumour types, pancreatic | Familial malignant melanoma |
| CDKN2C | 1031 | 1p32 | glioma, MM | |
| CDX2 | 1045 | 13q12.3 | AML | |
| CEBPA | 1050 | 19q13.1 | AML, MDS | |
| CEP1 | 11064 | 9q33 | MPD, NHL | |
| CHCHD7 | 79145 | 8q11.2 | salivary adenoma | |
| CHEK2 | 11200 | 22q12.1 | breast | familial breast cancer |
| CHIC2 | 26511 | 4q11-q12 | AML | |
| CHN1 | 1123 | 2q31-q32.1 | extraskeletal myxoid chondrosarcoma | |
| CIC | 23152 | 19q13.2 | soft tissue sarcoma | |
| CLTC | 1213 | 17q11-qter | ALCL, renal | |

TABLE 2-continued

Cancer-specific mutations for various cancers.

| Symbol | GeneID | Chr Band | Tumour Types (Somatic Mutations) | Cancer Syndrome |
|---|---|---|---|---|
| CLTCL1 | 8218 | 22q11.21 | ALCL | |
| CMKOR1 | 57007 | 2q37.3 | lipoma | |
| COL1A1 | 1277 | 17q21.31-q22 | dermatofibrosarcoma protuberans, aneurysmal bone cyst | |
| COPEB | 1316 | 10p15 | prostate, glioma | |
| COX6C | 1345 | 8q22-q23 | uterine leiomyoma | |
| CREB1 | 1385 | 2q34 | clear cell sarcoma, angiomatoid fibrous histiocytoma | |
| CREB3L2 | 64764 | 7q34 | fibromyxoid sarcoma | |
| CREBBP | 1387 | 16p13.3 | AL, AML | |
| CRLF2 | 64109 | Xp22.3; Yp11.3 | B-ALL, Downs associated ALL | |
| CRTC3 | 64784 | 15q26.1 | salivary gland mucoepidermoid | |
| CTNNB1 | 1499 | 3p22-p21.3 | colorectal, ovarian, hepatoblastoma, others, pleomorphic salivary adenoma | |
| CYLD | 1540 | 16q12-q13 | cylindroma | Familial cylindromatosis |
| D10S170 | 8030 | 10q21 | papillary thyroid, CML | |
| DDB2 | 1643 | 11p12 | skin basal cell, skin squamous cell, melanoma | Xeroderma pigmentosum (E) |
| DDIT3 | 1649 | 12q13.1-q13.2 | liposarcoma | |
| DDX10 | 1662 | 11q22-q23 | AML* | |
| DDX5 | 1655 | 17q21 | prostate | |
| DDX6 | 1656 | 11q23.3 | B-NHL | |
| DEK | 7913 | 6p23 | AML | |
| DICER1 | 23405 | 14q32.13 | pleuropulmonary blastoma | Familial Pleuropulmonary Blastoma |
| DUX4 | 22947 | 4q35 | soft tissue sarcoma | |
| EGFR | 1956 | 7p12.3-p12.1 | glioma, NSCLC | Familial lung cancer |
| EIF4A2 | 1974 | 3q27.3 | NHL | |
| ELF4 | 2000 | Xq26 | AML | |
| ELK4 | 2005 | 1q32 | prostate | |
| ELKS | 23085 | 12p13.3 | papillary thyroid | |
| ELL | 8178 | 19p13.1 | AL | |
| ELN | 2006 | 7q11.23 | B-ALL | |
| EML4 | 27436 | 2p21 | NSCLC | |
| EP300 | 2033 | 22q13 | colorectal, breast, pancreatic, AML | |
| EPS15 | 2060 | 1p32 | ALL | |
| ERBB2 | 2064 | 17q21.1 | breast, ovarian, other tumour types, NSCLC, gastric | |
| ERCC2 | 2068 | 19q13.2-q13.3 | skin basal cell, skin squamous cell, melanoma | Xeroderma pigmentosum (D) |
| ERCC3 | 2071 | 2q21 | skin basal cell, skin squamous cell, melanoma | Xeroderma pigmentosum (B) |
| ERCC4 | 2072 | 16p13.3-p13.13 | skin basal cell, skin squamous cell, melanoma | Xeroderma pigmentosum (F) |
| ERCC5 | 2073 | 13q33 | skin basal cell, skin squamous cell, melanoma | Xeroderma pigmentosum (G) |
| ERG | 2078 | 21q22.3 | Ewing sarcoma, prostate, AML | |
| ETV1 | 2115 | 7p22 | Ewing sarcoma, prostate | |
| ETV4 | 2118 | 17q21 | Ewing sarcoma, Prostate carcinoma | |
| ETV5 | 2119 | 3q28 | Prostate | |
| ETV6 | 2120 | 12p13 | congenital fibrosarcoma, multiple leukemia and lymphoma, secretory breast, MDS, ALL | |
| EVI1 | 2122 | 3q26 | AML, CML | |
| EWSR1 | 2130 | 22q12 | Ewing sarcoma, desmoplastic small round cell tumor, ALL, clear cell sarcoma, sarcoma, myoepithelioma | |
| EXT1 | 2131 | 8q24.11-q24.13 | exostoses, osteosarcoma | Multiple Exostoses Type 1 |
| EXT2 | 2132 | 11p12-p11 | exostoses, osteosarcoma | Multiple Exostoses Type 2 |
| EZH2 | 2146 | 7q35-q36 | DLBCL | |
| FACL6 | 23305 | 5q31 | AML, AEL | |
| FANCA | 2175 | 16q24.3 | AML, leukemia | Fanconi anaemia A |
| FANCC | 2176 | 9q22.3 | AML, leukemia | Fanconi anaemia C |
| FANCD2 | 2177 | 3p26 | AML, leukemia | Fanconi anaemia D2 |
| FANCE | 2178 | 6p21-p22 | AML, leukemia | Fanconi anaemia E |
| FANCF | 2188 | 11p15 | AML, leukemia | Fanconi anaemia F |
| FANCG | 2189 | 9p13 | AML, leukemia | Fanconi anaemia G |
| FBXW7 | 55294 | 4q31.3 | colorectal, endometrial, T-ALL | |
| FCGR2B | 2213 | 1q23 | ALL | |
| FEV | 54738 | 2q36 | Ewing sarcoma | |
| FGFR1 | 2260 | 8p11.2-p11.1 | MPD, NHL | |
| FGFR1OP | 11116 | 6q27 | MPD, NHL | |
| FGFR2 | 2263 | 10q26 | gastric. NSCLC, endometrial | |
| FGFR3 | 2261 | 4p16.3 | bladder, MM, T-cell lymphoma | |
| FH | 2271 | 1q42.1 | lieomyomatosis, renal | hereditary leiomyomatosis and renal cell cancer |

TABLE 2-continued

Cancer-specific mutations for various cancers.

| Symbol | GeneID | Chr Band | Tumour Types (Somatic Mutations) | Cancer Syndrome |
|---|---|---|---|---|
| FIP1L1 | 81608 | 4q12 | idiopathic hypereosinophilic syndrome | |
| FLI1 | 2313 | 11q24 | Ewing sarcoma | |
| FLT3 | 2322 | 13q12 | AML, ALL | |
| FNBP1 | 23048 | 9q23 | AML | |
| FOXL2 | 668 | 3q23 | granulosa-cell tumour of the ovary | |
| FOXO1A | 2308 | 13q14.1 | alveolar rhabdomyosarcomas | |
| FOXO3A | 2309 | 6q21 | AL | |
| FOXP1 | 27086 | 3p14.1 | ALL | |
| FSTL3 | 10272 | 19p13 | B-CLL | |
| FUS | 2521 | 16p11.2 | liposarcoma, AML, Ewing sarcoma, angiomatoid fibrous histiocytoma, fibromyxoid sarcoma | |
| FVT1 | 2531 | 18q21.3 | B-NHL | |
| GAS7 | 8522 | 17p | AML* | |
| GATA1 | 2623 | Xp11.23 | megakaryoblastic leukemia of Downs Syndrome | |
| GATA2 | 2624 | 3q21.3 | AML(CML blast transformation) | |
| GATA3 | 2625 | 10p15 | breast | |
| GMPS | 8833 | 3q24 | AML | |
| GNAQ | 2776 | 9q21 | uveal melanoma | |
| GNAS | 2778 | 20q13.2 | pituitary adenoma | |
| GOLGA5 | 9950 | 14q | papillary thyroid | |
| GOPC | 57120 | 6q21 | glioblastoma | |
| GPC3 | 2719 | Xq26.1 | Wilms tumour | Simpson-Golabi-Behmel syndrome |
| GPHN | 10243 | 14q24 | AL | |
| GRAF | 23092 | 5q31 | AML, MDS | |
| HCMOGT-1 | 92521 | 17p11.2 | JMML | |
| HEAB | 10978 | 11q12 | AML | |
| HEI10 | 57820 | 14q11.1 | uterine leiomyoma | |
| HERPUD1 | 9709 | 16q12.2-q13 | prostate | |
| HIP1 | 3092 | 7q11.23 | CMML | |
| HIST1H4I | 8294 | 6p21.3 | NHL | |
| HLF | 3131 | 17q22 | ALL | |
| HLXB9 | 3110 | 7q36 | AML | |
| HMGA1 | 3159 | 6p21 | microfollicular thyroid adenoma, various benign mesenchymal tumors | |
| HMGA2 | 8091 | 12q15 | lipoma | |
| HNRNPA2B1 | 3181 | 7p15 | prostate | |
| HOOK3 | 84376 | 8p11.21 | papillary thyroid | |
| HOXA11 | 3207 | 7p15-p14.2 | CML | |
| HOXA13 | 3209 | 7p15-p14.2 | AML | |
| HOXA9 | 3205 | 7p15-p14.2 | AML* | |
| HOXC11 | 3227 | 12q13.3 | AML | |
| HOXC13 | 3229 | 12q13.3 | AML | |
| HOXD11 | 3237 | 2q31-q32 | AML | |
| HOXD13 | 3239 | 2q31-q32 | AML* | |
| HRAS | 3265 | 11p15.5 | infrequent sarcomas, rare other types, rhadomyosarcoma, ganglioneuroblastoma, bladder | Costello syndrome |
| HRPT2 | 3279 | 1q21-q31 | parathyroid adenoma, mulitple ossifying jaw fibroma | Hyperparathyroidism-jaw tumor syndrome |
| HSPCA | 3320 | 14q32.31 | NHL | |
| HSPCB | 3326 | 6p12 | NHL | |
| IDH1 | 3417 | 2q33.3 | gliobastoma | |
| IDH2 | 3418 | 15q26.1 | GBM | |
| IGH@ | 3492 | 14q32.33 | MM, Burkitt lymphoma, NHL, CLL, B-ALL, MALT, MLCLS | |
| IGK@ | 50802 | 2p12 | Burkitt lymphoma, B-NHL | |
| IGL@ | 3535 | 22q11.1-q11.2 | Burkitt lymphoma | |
| IKZF1 | 10320 | 7p12.2 | ALL | |
| IL2 | 3558 | 4q26-q27 | intestinal T-cell lymphoma | |
| IL21R | 50615 | 16p11 | NHL | |
| IL6ST | 3572 | 5q11 | hepatocellular ca | |
| IRF4 | 3662 | 6p25-p23 | MM | |
| IRTA1 | 83417 | 1q21 | B-NHL | |
| ITK | 3702 | 5q31-q32 | peripheral T-cell lymphoma | |
| JAK1 | 3716 | 1p32.3-p31.3 | ALL | |
| JAK2 | 3717 | 9p24 | ALL, AML, MPD, CML | |
| JAK3 | 3718 | 19p13.1 | acute megakaryocytic leukemia, | |
| JAZF1 | 221895 | 7p15.2-p15.1 | endometrial stromal tumours | |
| JUN | 3725 | 1p32-p31 | sarcoma | |
| KDM5A | 5927 | 12p11 | AML | |
| KDM5C | 8242 | Xp11.22-p11.21 | clear cell renal carcinoma | |
| KDM6A | 7403 | Xp11.2 | renal, oesophageal SCC, MM | |
| KDR | 3791 | 4q11-q12 | NSCLC, angiosarcoma | |

TABLE 2-continued

Cancer-specific mutations for various cancers.

| Symbol | GeneID | Chr Band | Tumour Types (Somatic Mutations) | Cancer Syndrome |
| --- | --- | --- | --- | --- |
| KIAA1549 | 57670 | 7q34 | pilocytic astrocytoma | |
| KIT | 3815 | 4q12 | GIST, AML, TGCT, mastocytosis, mucosal melanoma, epithelioma | Familial gastrointestinal stromal tumour |
| KLK2 | 3817 | 19q13.41 | prostate | |
| KRAS | 3845 | 12p12.1 | pancreatic, colorectal, lung, thyroid, AML, others | |
| KTN1 | 3895 | 14q22.1 | papillary thryoid | |
| LAF4 | 3899 | 2q11.2-q12 | ALL, T-ALL | |
| LASP1 | 3927 | 17q11-q21.3 | AML | |
| LCK | 3932 | 1p35-p34.3 | T-ALL | |
| LCP1 | 3936 | 13q14.1-q14.3 | NHL | |
| LCX | 80312 | 10q21 | AML | |
| LHFP | 10186 | 13q12 | lipoma | |
| LIFR | 3977 | 5p13-p12 | salivary adenoma | |
| LMO1 | 4004 | 11p15 | T-ALL | |
| LMO2 | 4005 | 11p13 | T-ALL | |
| LPP | 4026 | 3q28 | lipoma, leukemia | |
| LYL1 | 4066 | 19p13.2-p13.1 | T-ALL | |
| MADH4 | 4089 | 18q21.1 | colorectal, pancreatic, small intestine, gastrointestinal polyps | Juvenile polyposis |
| MAF | 4094 | 16q22-q23 | MM | |
| MAFB | 9935 | 20q11.2-q13.1 | MM | |
| MALT1 | 10892 | 18q21 | MALT | |
| MAML2 | 84441 | 11q22-q23 | salivary gland mucoepidermoid | |
| MAP2K4 | 6416 | 17p11.2 | pancreatic, breast, colorectal | |
| MDM2 | 4193 | 12q15 | sarcoma, glioma, colorectal, other | |
| MDM4 | 4194 | 1q32 | GBM, bladder, retinoblastoma | |
| MDS1 | 4197 | 3q26 | MDS, AML | |
| MDS2 | 259283 | 1p36 | MDS | |
| MECT1 | 94159 | 19p13 | salivary gland mucoepidermoid | |
| MEN1 | 4221 | 11q13 | parathyroid tumors, parathyroid adenoma, pituitary adenoma, pancreatic islet cell, carcinoid | Multiple Endocrine Neoplasia Type 1 |
| MET | 4233 | 7q31 | papillary renal, head-neck squamous cell | Familial Papillary Renal Cancer |
| MHC2TA | 4261 | 16p13 | NHL | |
| MITF | 4286 | 3p14.1 | melanoma | |
| MKL1 | 57591 | 22q13 | acute megakaryocytic leukemia | |
| MLF1 | 4291 | 3q25.1 | AML | |
| MLH1 | 4292 | 3p21.3 | colorectal, endometrial, ovarian, CNS | Hereditary non-polyposis colorectal cancer, Turcot syndrome |
| MLL | 4297 | 11q23 | AML, ALL | |
| MLLT1 | 4298 | 19p13.3 | AL | |
| MLLT10 | 8028 | 10p12 | AL | |
| MLLT2 | 4299 | 4q21 | AL | |
| MLLT3 | 4300 | 9p22 | ALL | |
| MLLT4 | 4301 | 6q27 | AL | |
| MLLT6 | 4302 | 17q21 | AL | |
| MLLT7 | 4303 | Xq13.1 | AL | |
| MN1 | 4330 | 22q13 | AML, meningioma | |
| MPL | 4352 | p34 | MPD | Familial essential thrombocythemia |
| MSF | 10801 | 17q25 | AML* | |
| MSH2 | 4436 | 2p22-p21 | colorectal, endometrial, ovarian | Hereditary non-polyposis colorectal cancer |
| MSH6 | 2956 | 2p16 | colorectal, endometrial, ovarian | Hereditary non-polyposis colorectal cancer |
| MSI2 | 124540 | 17q23.2 | CML | |
| MSN | 4478 | Xq11.2-q12 | ALCL | |
| MTCP1 | 4515 | Xq28 | T cell prolymphocytic leukemia | |
| MUC1 | 4582 | 1q21 | B-NHL | |
| MUTYH | 4595 | 1p34.3-1p32.1 | colorectal | Adenomatous polyposis coli |
| MYB | 4602 | 6q22-23 | adenoid cystic carcinoma | |
| MYC | 4609 | 8q24.12-q24.13 | Burkitt lymphoma, amplified in other cancers, B-CLL | |
| MYCL1 | 4610 | 1p34.3 | small cell lung | |
| MYCN | 4613 | 2p24.1 | neuroblastoma | |
| MYH11 | 4629 | 16p13.13-p13.12 | AML | |
| MYH9 | 4627 | 22q13.1 | ALCL | |
| MYST4 | 23522 | 10q22 | AML | |
| NACA | 4666 | 12q23-q24.1 | NHL | |
| NBS1 | 4683 | 8q21 | NHL, glioma, medulloblastoma, rhabdomyosarcoma | Nijmegen breakage syndrome |
| NCOA1 | 8648 | 2p23 | alveolar rhadomyosarcoma | |
| NCOA2 | 10499 | 8q13.1 | AML | |
| NCOA4 | 8031 | 10q11.2 | papillary thyroid | |

TABLE 2-continued

Cancer-specific mutations for various cancers.

| Symbol | GeneID | Chr Band | Tumour Types (Somatic Mutations) | Cancer Syndrome |
|---|---|---|---|---|
| NF1 | 4763 | 17q12 | neurofibroma, glioma | Neurofibromatosis type 1 |
| NF2 | 4771 | 22q12.2 | meningioma, acoustic neuroma, renal | Neurofibromatosis type 2 |
| NFIB | 4781 | 9p24.1 | adenoid cystic carcinoma, lipoma | |
| NFKB2 | 4791 | 10q24 | B-NHL | |
| NIN | 51199 | 14q24 | MPD | |
| NONO | 4841 | Xq13.1 | papillary renal cancer | |
| NOTCH1 | 4851 | 9q34.3 | T-ALL | |
| NOTCH2 | 4853 | 1p13-p11 | marginal zone lymphoma, DLBCL | |
| NPM1 | 4869 | 5q35 | NHL, APL, AML | |
| NR4A3 | 8013 | 9q22 | extraskeletal myxoid chondrosarcoma | |
| NRAS | 4893 | 1p13.2 | melanoma, MM, AML, thyroid | |
| NSD1 | 64324 | 5q35 | AML | |
| NTRK1 | 4914 | 1q21-q22 | papillary thyroid | |
| NTRK3 | 4916 | 15q25 | congenital fibrosarcoma, Secretory breast | |
| NUMA1 | 4926 | 11q13 | APL | |
| NUP214 | 8021 | 9q34.1 | AML, T-ALL | |
| NUP98 | 4928 | 11p15 | AML | |
| NUT | 256646 | q13 | lethal midline carcinoma of young people | |
| OLIG2 | 10215 | 21q22.11 | T-ALL | |
| OMD | 4958 | 9q22.31 | aneurysmal bone cysts | |
| P2RY8 | 286530 | Xp22.3; Yp11.3 | B-ALL, Downs associated ALL | |
| PAFAH1B2 | 5049 | 11q23 | MLCLS | |
| PALB2 | 79728 | 16p12.1 | Wilms tumor, medulloblastoma, AML, breast | Fanconi anaemia N, breast cancer susceptibility |
| PAX3 | 5077 | 2q35 | alveolar rhabdomyosarcoma | |
| PAX5 | 5079 | 9p13 | NHL, ALL, B-ALL | |
| PAX7 | 5081 | 1p36.2-p36.12 | alveolar rhabdomyosarcoma | |
| PAX8 | 7849 | 2q12-q14 | follicular thyroid | |
| PBX1 | 5087 | 1q23 | pre B-ALL, myoepithelioma | |
| PCM1 | 5108 | 8p22-p21.3 | papillary thyroid, CML, MPD | |
| PCSK7 | 9159 | 11q23.3 | MLCLS | |
| PDE4DIP | 9659 | 1q12 | MPD | |
| PDGFB | 5155 | 22q12.3-q13.1 | DFSP | |
| PDGFRA | 5156 | 4q11-q13 | GIST, idiopathic hypereosinophilic syndrome | |
| PDGFRB | 5159 | 5q31-q32 | MPD, AML, CMML, CML | |
| PER1 | 5187 | 17p13.1-17p12 | AML, CMML | |
| PHOX2B | 8929 | 4p12 | neuroblastoma | familial neuroblastoma |
| PICALM | 8301 | 11q14 | TALL, AML, | |
| PIK3CA | 5290 | 3q26.3 | colorectal, gastric, gliobastoma, breast | |
| PIK3R1 | 5295 | 5q13.1 | gliobastoma, ovarian, colorectal | |
| PIM1 | 5292 | 6p21.2 | NHL | |
| PLAG1 | 5324 | 8q12 | salivary adenoma | |
| PML | 5371 | 15q22 | APL, ALL | |
| PMS1 | 5378 | 2q31-q33 | colorectal, endometrial, ovarian | Hereditary non-polyposis colorectal cancer |
| PMS2 | 5395 | 7p22 | colorectal, endometrial, ovarian, medulloblastoma, glioma | Hereditary non-polyposis colorectal cancer, Turcot syndrome |
| PMX1 | 5396 | 1q24 | AML | |
| PNUTL1 | 5413 | 22q11.2 | AML | |
| POU2AF1 | 5450 | 11q23.1 | NHL | |
| POU5F1 | 5460 | 6p21.31 | sarcoma | |
| PPARG | 5468 | 3p25 | follicular thyroid | |
| PRCC | 5546 | 1q21.1 | papillary renal | |
| PRDM16 | 63976 | 1p36.23-p33 | MDS, AML | |
| PRF1 | 5551 | 10q22 | various leukaemia, lymphoma | |
| PRKAR1A | 5573 | 17q23-q24 | myxoma, endocrine, papillary thyroid | Carney complex |
| PRO1073 | 29005 | 11q31.1 | renal cell carcinoma (childhood epithelioid) | |
| PSIP2 | 11168 | 9p22.2 | AML | |
| PTCH | 5727 | 9q22.3 | skin basal cell, medulloblastoma | Nevoid Basal Cell Carcinoma Syndrome |
| PTEN | 5728 | 10q23.3 | harmatoma, glioma, prostate, endometrial | Cowden Syndrome, Bannayan-Riley-Ruvalcaba syndrome |
| PTPN11 | 5781 | 12q24.1 | JMML, AML, MDS | |
| RAB5EP | 9135 | 17p13 | CMML | |
| RAD51L1 | 5890 | 14q23-q24.2 | lipoma, uterine leiomyoma | |
| RAF1 | 5894 | 3p25 | pilocytic astrocytoma | |
| RANBP17 | 64901 | 5q34 | ALL | |
| RAP1GDS1 | 5910 | 4q21-q25 | T-ALL | |
| RARA | 5914 | 17q12 | APL | |
| RB1 | 5925 | 13q14 | retinoblastoma, sarcoma, breast, small cell lung | Familial retinoblastoma |
| RBM15 | 64783 | 1p13 | acute megakaryocytic leukemia | |

TABLE 2-continued

Cancer-specific mutations for various cancers.

| Symbol | GeneID | Chr Band | Tumour Types (Somatic Mutations) | Cancer Syndrome |
|---|---|---|---|---|
| RECQL4 | 9401 | 8q24.3 | osteosarcoma, skin basal and sqamous cell | Rothmund-Thompson Syndrome |
| REL | 5966 | 2p13-p12 | Hodgkin Lymphoma | |
| RET | 5979 | 10q11.2 | medullary thyroid, papillary thyroid, pheochromocytoma | Multiple endocrine neoplasia 2A/2B |
| ROS1 | 6098 | 6q22 | glioblastoma, NSCLC | |
| RPL22 | 6146 | 1p36.31 | AML, CML | |
| RPN1 | 6184 | 3q21.3-q25.2 | AML | |
| RUNX1 | 861 | 21q22.3 | AML, preB- ALL, T-ALL | |
| RUNXBP2 | 7994 | 8p11 | AML | |
| SBDS | 51119 | 7q11 | AML, MDS | Schwachman-Diamond syndrome |
| SDH5 | 54949 | 11q12.2 | paraganglioma | Familial paraganglioma |
| SDHB | 6390 | 1p36.1-p35 | paraganglioma, pheochromocytoma | Familial paraganglioma |
| SDHC | 6391 | 1q21 | paraganglioma, pheochromocytoma | Familial paraganglioma |
| SDHD | 6392 | 11q23 | paraganglioma, pheochromocytoma | Familial paraganglioma |
| SEPT6 | 23157 | Xq24 | AML | |
| SET | 6418 | 9q34 | AML | |
| SETD2 | 29072 | 3p21.31 | clear cell renal carcinoma | |
| SFPQ | 6421 | 1p34.3 | papillary renal cell | |
| SFRS3 | 6428 | 6p21 | follicular lymphoma | |
| SH3GL1 | 6455 | 19p13.3 | AL | |
| SIL | 6491 | 1p32 | T-ALL | |
| SLC45A3 | 85414 | 1q32 | prostate | |
| SMARCA4 | 6597 | 19p13.2 | NSCLC | |
| SMARCB1 | 6598 | 22q11 | malignant rhabdoid | Rhabdoid predisposition syndrome |
| SMO | 6608 | 7q31-q32 | skin basal cell | |
| SOCS1 | 8651 | 16p13.13 | Hodgkin Lymphoma, PMBL | |
| SRGAP3 | 9901 | 3p25.3 | pilocytic astrocytoma | |
| SS18 | 6760 | 18q11.2 | synovial sarcoma | |
| SS18L1 | 26039 | 20q13.3 | synovial sarcoma | |
| SSH3BP1 | 10006 | 10p11.2 | AML | |
| SSX1 | 6756 | Xp11.23-p11.22 | synovial sarcoma | |
| SSX2 | 6757 | Xp11.23-p11.22 | synovial sarcoma | |
| SSX4 | 6759 | Xp11.23 | synovial sarcoma | |
| STK11 | 6794 | 19p13.3 | NSCLC, pancreatic, jejunal harmartoma, ovarian, testicular | Peutz-Jeghers syndrome |
| STL | 7955 | 6q23 | B-ALL | |
| SUFU | 51684 | 10q24.32 | medulloblastoma | Medulloblastoma predisposition |
| SUZ12 | 23512 | 17q11.2 | endometrial stromal tumours | |
| SYK | 6850 | 9q22 | MDS, peripheral T-cell lymphoma | |
| TAF15 | 8148 | 17q11.1-q11.2 | extraskeletal myxoid chondrosarcomas, ALL | |
| TAL1 | 6886 | 1p32 | lymphoblastic leukemia/biphasic | |
| TAL2 | 6887 | 9q31 | T-ALL | |
| TCEA1 | 6917 | 8q11.2 | salivary adenoma | |
| TCF1 | 6927 | 12q24.2 | hepatic adenoma, hepatocellular ca | Familial Hepatic Adenoma |
| TCF12 | 6938 | 15q21 | extraskeletal myxoid chondrosarcoma | |
| TCF3 | 6929 | 19p13.3 | pre B-ALL | |
| TCL1A | 8115 | 14q32.1 | T-CLL | |
| TCL6 | 27004 | 14q32.1 | T-ALL | |
| TET2 | 54790 | 4q24 | MDS | |
| TFE3 | 7030 | Xp11.22 | papillary renal, alveolar soft part sarcoma, renal | |
| TFEB | 7942 | 6p21 | renal (childhood epithelioid) | |
| TFG | 10342 | 3q11-q12 | papillary thyroid, ALCL, NSCLC | |
| TFPT | 29844 | 19q13 | pre-B ALL | |
| TFRC | 7037 | 3q29 | NHL | |
| THRAP3 | 9967 | 1p34.3 | aneurysmal bone cysts | |
| TIF1 | 8805 | 7q32-q34 | APL | |
| TLX1 | 3195 | 10q24 | T-ALL | |
| TLX3 | 30012 | 5q35.1 | T-ALL | |
| TMPRSS2 | 7113 | 21q22.3 | prostate | |
| TNFAIP3 | 7128 | 6q23 | marginal zone B-cell lymphomas, Hodgkin's lymphoma, primary mediastinal B cell lymphoma | |
| TNFRSF17 | 608 | 16p13.1 | intestinal T-cell lymphoma | |
| TNFRSF6 | 355 | 10q24.1 | TGCT, nasal NK/T lymphoma, skin squamous cell ca -burn scar-related | |
| TOP1 | 7150 | 20q12-q13.1 | AML* | |
| TP53 | 7157 | 17p13 | breast, colorectal, lung, sarcoma, adrenocortical, glioma, multiple other tumour types | Li-Fraumeni syndrome |
| TPM3 | 7170 | 1q22-q23 | papillary thyroid, ALCL | |
| TPM4 | 7171 | 19p13.1 | ALCL | |

TABLE 2-continued

Cancer-specific mutations for various cancers.

| Symbol | GeneID | Chr Band | Tumour Types (Somatic Mutations) | Cancer Syndrome |
|---|---|---|---|---|
| TPR | 7175 | 1q25 | papillary thyroid | |
| TRA@ | 6955 | 14q11.2 | T-ALL | |
| TRB@ | 6957 | 7q35 | T-ALL | |
| TRD@ | 6964 | 14q11 | T-cell leukemia | |
| TRIM27 | 5987 | 6p22 | papillary thyroid | |
| TRIM33 | 51592 | 1p13 | papillary thyroid | |
| TRIP11 | 9321 | 14q31-q32 | AML | |
| TSC1 | 7248 | 9q34 | hamartoma, renal cell | Tuberous sclerosis 1 |
| TSC2 | 7249 | 16p13.3 | hamartoma, renal cell | Tuberous sclerosis 2 |
| TSHR | 7253 | 14q31 | toxic thyroid adenoma | |
| TTL | 150465 | 2q13 | ALL | |
| USP6 | 9098 | 17p13 | aneurysmal bone cysts | |
| VHL | 7428 | 3p25 | renal, hemangioma, pheochromocytoma | von Hippel-Lindau syndrome |
| WAS | 7454 | Xp11.23-p11.22 | lymphoma | Wiskott-Aldrich syndrome |
| WHSC1 | 7468 | 4p16.3 | MM | |
| WHSC1L1 | 54904 | 8p12 | AML | |
| WRN | 7486 | 8p12-p11.2 | osteosarcoma, meningioma, others | Werner Syndrome |
| WT1 | 7490 | 11p13 | Wilms, desmoplastic small round cell tumor | Denys-Drash syndrome, Frasier syndrome, Familial Wilms tumor |
| WTX | 139285 | Xq11.1 | Wilms tumour | |
| XPA | 7507 | 9q22.3 | skin basal cell, skin squamous cell, melanoma | Xeroderma pigmentosum (A) |
| XPC | 7508 | 3p25 | skin basal cell, skin squamous cell, melanoma | Xeroderma pigmentosum (C) |
| ZNF145 | 7704 | 11q23.1 | APL | |
| ZNF198 | 7750 | 13q11-q12 | MPD, NHL | |
| ZNF278 | 23598 | 22q12-q14 | Ewing sarcoma | |
| ZNF331 | 55422 | 19q13.3-q13.4 | follicular thyroid adenoma | |
| ZNF384 | 171017 | 12p13 | ALL | |
| ZNF521 | 25925 | 18q11.2 | ALL | |
| ZNF9 | 7555 | 3q21 | aneurysmal bone cysts | |
| ZNFN1A1 | 10320 | 7p12 | ALL, DLBL | |

Example 2

Introduction

Diagnostic platforms which are highly predictive for diagnosing, monitoring, and stratifying cancer patients are key instruments in the development of personalized medicine. In this Example, it is demonstrated that tumor cells transfer (mutant) RNA into blood platelets in vitro, and it is shown that blood platelets isolated from glioblastoma and prostate cancer patients contain the cancer-associated RNA biomarkers EGFRvIII, and PCA3 and PSA, respectively. Moreover, gene expression arrays revealed a distinct mRNA signature in platelets from glioma patients as compared to normal control subjects. Because platelets are easily accessible and isolated, they may form an attractive platform for the companion diagnostics of cancer.

Methods

Platelet Isolation and Tissue Resection.

Platelets were isolated from whole blood collected in purple-cap BD Vacutainers containing EDTA anti-coagulant by standard centrifugation, and quality (activation and aggregation) as well as purity was assessed by microscopic analysis showing less than 0.1% contamination with red or white blood cells. Next, isolated platelet pellets were snap-frozen for further use. Glioma tissue resection and whole blood harvesting from glioma and prostate cancer patients was performed at the VU University medical center and Umeå University, as described elsewhere (J. Skog et al., Nat Cell Biol. 10(12), 1470-6 (2008)).

Microvesicle Isolation, Labeling, and Transfer.

Microvesicles were isolated from U87-EGFRvIII glioma cells and labeled as described previously (J. Skog et al., Nat Cell Biol. 10(12), 1470-6 (2008)). After U87-dEGFR microvesicle incubation the platelets were washed and treated with RNAse enzymes to ensure the EGFRvIII RNA was delivered into the platelets and therefore protected from RNAse-mediated degradation. For confocal microscopy analysis the platelets were stained with texas red-conjugated wheat germ agglutinin to indicate platelet structure and analyzed for microvesicle uptake by the presence of green PKH67. RNA purification. RNA was isolated using miRvana (Ambion) or miRNeasy (Qiagen) protocols according the manufacturer's instruction. RNA concentration and quality was determined using a Bioanalyzer 2100 with total RNA Pico chip (Agilent).

RT-PCR.

RT-PCR for EGFRvIII, PCA3, PSA, and GAPDH, was performed as described previously (J. Skog et al., Nat Cell Biol. 10(12), 1470-6 (2008)) using the following primer sets:

```
GAPDH primers:
                              (SEQ ID NO: 1)
forward     5'-GAAGGTGAAGGTCGGAGTC-3',
                              (SEQ ID NO: 2)
reverse:    5'-TCAGAAGATGGTGATGGGATTTC-3'.

PSA primers:
                              (SEQ ID NO: 3)
forward     5'-ATGTGGGTCCCGGTTGTCTT-3',
                              (SEQ ID NO: 4)
reverse     5'-TCCCACAATCCGAGACAGGA-3'.
```

-continued

```
Nested PCA3 primers:
PCR1:
                                         (SEQ ID NO: 5)
forward      5'-AGTCCGCTGTGAGTCT-3',
                                         (SEQ ID NO: 6)
reverse      5'-CCATTTCAGCAGATGTGTGG-3';

PCR2:
                                         (SEQ ID NO: 7)
forward      5'-ATCGACGGCACTTTCTGAGT-3',
                                         (SEQ ID NO: 8)
reverse      5'-TGTGTGGCCTCAGATGGTAA-3'.

Nested EGFRvIII primers:
PCR1:
                                         (SEQ ID NO: 9)
forward      5'-CCAGTATTGATCGGGAGAGC-3',
                                         (SEQ ID NO: 10)
reverse      5'-TGTGGATCCAGAGGAGGAGT-3';

PCR2:
                                         (SEQ ID NO: 11)
forward      5'-GAGCTCTTCGGGGAGCAG-3',
                                         (SEQ ID NO: 12)
reverse      5'-GCCCTTCGCACTTCTTACAC-3'.
```

Gene Expression Arrays.

The mRNA expression arrays were performed at the VU University Medical Center microarray core facility using Agilent 4×44K gene expression arrays. Platelet RNA integrity was assessed using the Agilent 2100 Bioanalyzer (Agilent Technologies, Inc.). RNA samples were labelled using the Agilent Low RNA Input Linear Amplification Kit Plus (5188-5340) according to the manufacturer's protocol.

Briefly, 25 ng of total RNA was amplified and reverse transcribed to cDNA using T7-polymerase and subsequently labelled with Cy3 or Cy5. Dye incorporation was measured using a Nanodrop ND-1000 spectrophotometer. Subsequently, cRNA was hybridized using the Agilent Gene Expression Hybridization Kit (5188-5242), according to the manufacturer's protocol. Briefly, 825 ng of Cy3 labelled cRNA was mixed with 825 ng of Cy5 labelled cRNA, fragmented for 30 min at 60° C. in the dark and hybridized on an Agilent Hybridization Chamber Gasket Slide (G2534-60011) in a rotation oven at 65° C. for 17 h. Slides scanned using an Agilent Microarray Scanner (G2565BA). Image analysis and array normalization was performed using feature extraction software version 9.5 (Agilent Technologies, Inc.). The Agilent GE2-v5_95 protocol was applied using default settings.

Statistical Analysis.

The heat map (FIG. 3C) of the gene expression data was generated using median centered arrays in Excel (Microsoft Office 2007 package) with the S.A.M. analysis plug-in, with a set false discovery rate <0.5%. The top-30 significantly differentially expressed genes are depicted using Heatmap Builder v1.1 software (King et al. Physiol Genomics. Sep. 21, 2005; 23(1):103-118)).

Results

In this Example it is shown that platelets isolated from healthy human control subjects have the ability to take up RNA-containing microvesicles derived from human brain tumor cells (glioma), and contain tumor-associated RNA, including mutant EGFRvIII. Uptake of PKH67 labelled glioma-derived microvesicles is demonstrated in blood platelets by FACS analysis and confocal microscopy. In addition, it was shown that microvesicle-mediated transfer of mutant EGFRvIII RNA into platelets from healthy control subjects by RT-PCR occurs. Furthermore, it is determined that circulating platelets isolated from glioma patients, contain RNA biomarkers (see FIG. 3B). RT-PCR was used to determine whether mutant EGFRvIII mRNA was found in resected high-grade glioma tissues (n=18) and the result was compared to platelets from the same patient and to platelets from healthy control subjects (n=30). The samples were coded and RT-PCR was performed in a blind assay. Four of the 18 (22.5%) glioma samples contained the EGFRvIII transcript, as observed before. Notably, EGFRvIII could be amplified from platelets in 3 out of these 4 EGFRvIII-positive patients (75%), and in none of the platelets of the healthy donors (n=12), whereas GAPDH mRNA was detected in all platelet samples. A possible false negative signal was detected in the platelets of one patient only, which may be contributed to inadequate processing of the blood sample. Conversely, one patient with EGFRvIII-negative tissue sample was EGFRvIII-positive in the platelet sample, most likely due to heterogeneous distribution of EGFRvIII positive foci in high-grade gliomas.

Figure 4:
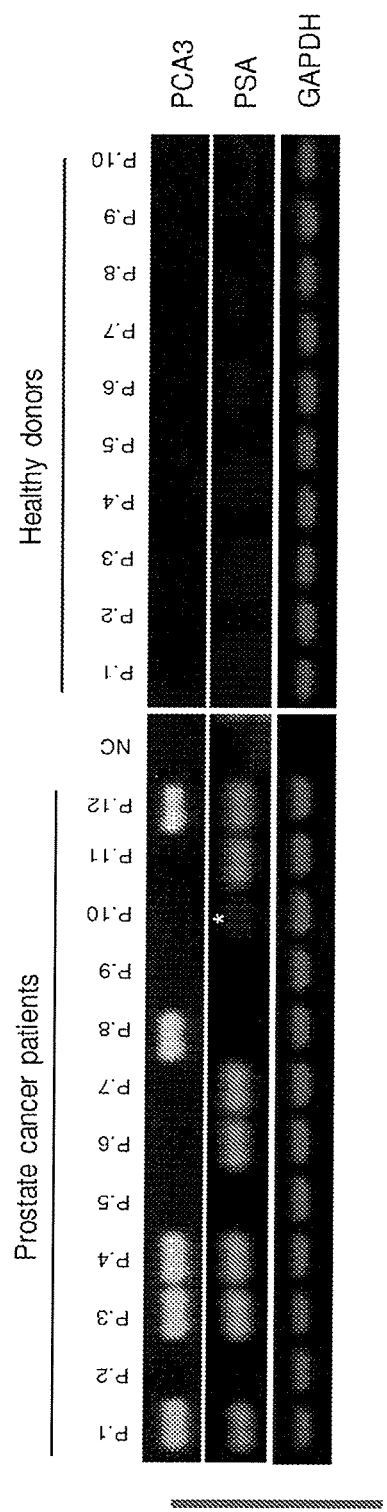
FIG. 4. RNA was isolated from platelets from healthy control subjects (n=8) and prostate cancer patients (n=12) and subjected to PCA3, PSA, and GAPDH RT-PCR analysis. * indicates weak positive signal.

To demonstrate that the presence of tumor-associated messages is not unique to platelets from glioma patients we report the presence of mRNAs coding for the prostate cancer markers PCA3 and PSA in platelets from prostate cancer patients (n=12) and their absence in platelets from healthy control subjects (n=10) (See FIG. 4). Finally, using gene expression arrays it was determined the mRNA expression profiles of platelets isolated from healthy control subjects (n=12), and glioma patients (n=8). Distinct mRNA expression profiles were obtained and a minimal glioma biomarker signature was detected (FIG. 3C, left panel). Interestingly, several of the potential biomarkers were barely detectable in control samples, whereas in the glioma samples they were highly expressed (FIG. 3C, right panel).

In conclusion, the findings of the present inventors demonstrate that blood platelets contain cancer markers in the form of tumor-derived or tumor-associated RNA and, therefore, may serve as a diagnostic platform for the molecular profiling of cancer in the context of personalized medicine.

The invention claimed is:

1. A method of quantifying RNA levels in a blood sample of a subject, said method comprising the steps of:
   a) isolating thrombocytes from the blood sample;
   b) extracting messenger ribonucleic acid (mRNA) from said thrombocytes to provide an extracted nucleic acid fraction from said thrombocytes;
   c) analyzing said extracted nucleic acid fraction by reverse transcribing extracted mRNA into cDNA, quantifying said cDNA to determine the amount of mRNA of at least three genes by conducting an amplification reaction which employs gene specific primers, wherein the at least three genes comprise genes encoding prostate cancer antigen 3, prostate-specific antigen, and epidermal growth factor receptor variant III.

2. The method of claim 1, wherein the primers for prostate specific antigen comprise SEQ ID NO: 3 and SEQ ID NO: 4.

3. The method of claim 1, wherein the primers for prostate cancer antigen 3 comprise SEQ ID NO: 5 and SEQ ID NO: 6.

4. The method of claim 1, wherein the primers for prostate cancer antigen 3 comprise SEQ ID NO: 7 and SEQ ID NO: 8.

5. The method of claim 1, wherein the primers for epidermal growth factor receptor variant III comprise SEQ ID NO: 9 and SEQ ID NO: 10.

6. The method of claim 1, wherein the primers for epidermal growth factor receptor variant III comprise SEQ ID NO: 11 and SEQ ID NO: 12.

* * * * *

SEQUENCE LISTING

```
<160> NUMBER OF SEQ ID NOS: 42

<210> SEQ ID NO 1
<211> LENGTH: 19
<212> TYPE: DNA
<213> ORGANISM: Artificial
<220> FEATURE:
<223> OTHER INFORMATION: primer

<400> SEQUENCE: 1
gaaggtgaag gtcggagtc                                               19
```

```
<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
tcagaagatg gtgatgggat ttc                                            23

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
atgtgggtcc cggttgtctt                                                20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
tcccacaatc cgagacagga                                                20

<210> SEQ ID NO 5
<211> LENGTH: 16
<212> TYPE: DNA
<213> ORGANISM: Artificial
<220> FEATURE:
<223> OTHER INFORMATION: primer

<400> SEQUENCE: 5
agtccgctgt gagtct                                                    16

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ccatttcagc agatgtgtgg                                                20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
atcgacggca ctttctgagt                                                20

<210> SEQ ID NO 8
<211> LENGTH: 20
<212> TYPE: DNA
<213> ORGANISM: Artificial
<220> FEATURE:
```

```
<223> OTHER INFORMATION: primer

<400> SEQUENCE: 8
tgtgtggcct cagatggtaa                                             20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
ccagtattga tcgggagagc                                             20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
tgtggatcca gaggaggagt                                             20

<210> SEQ ID NO 11
<211> LENGTH: 18
<212> TYPE: DNA
<213> ORGANISM: Artificial
<220> FEATURE:
<223> OTHER INFORMATION: primer

<400> SEQUENCE: 11
gagctcttcg gggagcag                                               18

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
gcccttcgca cttcttacac                                             20

<210> SEQ ID NO 13
<211> LENGTH: 60
<212> TYPE: DNA
<213> ORGANISM: Artificial
<220> FEATURE:
<223> OTHER INFORMATION: probe

<400> SEQUENCE: 13
aagcagctag gttgcaagaa cattcctcta ctttctgcta agccttggaa acagttggga     60

<210> SEQ ID NO 14
<211> LENGTH: 60
<212> TYPE: DNA
<213> ORGANISM: Artificial
<220> FEATURE:
<223> OTHER INFORMATION: probe

<400> SEQUENCE: 14
catcgtgggt ctcatgcacg tcaagacctt cccacatcca aactcagctt ccagcaggga     60
```

```
<210> SEQ ID NO 15
<211> LENGTH: 60
<212> TYPE: DNA
<213> ORGANISM: Artificial
<220> FEATURE:
<223> OTHER INFORMATION: probe

<400> SEQUENCE: 15
caattcaggg tccctggaga tcatcctaac aatgtggggc tgttaggttt tacctttgaa      60

<210> SEQ ID NO 16
<211> LENGTH: 60
<212> TYPE: DNA
<213> ORGANISM: Artificial
<220> FEATURE:
<223> OTHER INFORMATION: probe

<400> SEQUENCE: 16
ctggaatatt gtgaatgact agggaggtgg ggtagagcac tctccgtcct gctgctggca      60

<210> SEQ ID NO 17
<211> LENGTH: 60
<212> TYPE: DNA
<213> ORGANISM: Artificial
<220> FEATURE:
<223> OTHER INFORMATION: probe

<400> SEQUENCE: 17
aggaagtctg atcaccagtt tgctgaggtc tagggacaat aagtacaagc aaatgctggt      60

<210> SEQ ID NO 18
<211> LENGTH: 60
<212> TYPE: DNA
<213> ORGANISM: Artificial
<220> FEATURE:
<223> OTHER INFORMATION: probe

<400> SEQUENCE: 18
tcaatctaag aaatggttta gttttctct ttagctctat ggcatttcac tcaagtggac      60

<210> SEQ ID NO 19
<211> LENGTH: 60
<212> TYPE: DNA
<213> ORGANISM: Artificial
<220> FEATURE:
<223> OTHER INFORMATION: probe

<400> SEQUENCE: 19
tggaatcagg agacaaagct accacatgtg gaaaggtact atgtgtccat gtcattcaaa      60

<210> SEQ ID NO 20
<211> LENGTH: 60
<212> TYPE: DNA
<213> ORGANISM: Artificial
<220> FEATURE:
<223> OTHER INFORMATION: probe

<400> SEQUENCE: 20
ggttaaaaag agcttggcat ctgaaaacag ggagtggtgt ggaggggaag cagcctccgt      60

<210> SEQ ID NO 21
<211> LENGTH: 60
<212> TYPE: DNA
<213> ORGANISM: Artificial
<220> FEATURE:
<223> OTHER INFORMATION: probe
```

<400> SEQUENCE: 21
cgatctaacc ccttacccat ctctctactg ctggactgtg gagggtcacc aggttgggaa     60

<210> SEQ ID NO 22
<211> LENGTH: 60
<212> TYPE: DNA
<213> ORGANISM: Artificial
<220> FEATURE:
<223> OTHER INFORMATION: probe

<400> SEQUENCE: 22
ggctgccatt aggaactgca tgcagttaag ccgtataacc tctctgattt ttagtttctc     60

<210> SEQ ID NO 23
<211> LENGTH: 60
<212> TYPE: DNA
<213> ORGANISM: Artificial
<220> FEATURE:
<223> OTHER INFORMATION: probe

<400> SEQUENCE: 23
agatcgcaat gaggagtagc agggtagctg gttgctagag ttacggtggg gatcagaaac     60

<210> SEQ ID NO 24
<211> LENGTH: 60
<212> TYPE: DNA
<213> ORGANISM: Artificial
<220> FEATURE:
<223> OTHER INFORMATION: probe

<400> SEQUENCE: 24
gcttgatctg acgctccttt tctaaataac ttggatggat tattcgtatt ttttggtaac     60

<210> SEQ ID NO 25
<211> LENGTH: 60
<212> TYPE: DNA
<213> ORGANISM: Artificial
<220> FEATURE:
<223> OTHER INFORMATION: probe

<400> SEQUENCE: 25
taggagtccc aattattttt gactagggga tggggacag ttgacatttc tggtcctaca     60

<210> SEQ ID NO 26
<211> LENGTH: 60
<212> TYPE: DNA
<213> ORGANISM: Artificial
<220> FEATURE:
<223> OTHER INFORMATION: probe

<400> SEQUENCE: 26
ttttgagtcc ggaaaaacag aattccaagt caaattctgt tccaattatc ctggccatcg     60

<210> SEQ ID NO 27
<211> LENGTH: 60
<212> TYPE: DNA
<213> ORGANISM: Artificial
<220> FEATURE:
<223> OTHER INFORMATION: probe

<400> SEQUENCE: 27
tatctcttct tccttttgta tcctccattg tatcttcata caaaggacag tacacacttg     60

<210> SEQ ID NO 28
<211> LENGTH: 60

```
<212> TYPE: DNA
<213> ORGANISM: Artificial
<220> FEATURE:
<223> OTHER INFORMATION: probe

<400> SEQUENCE: 28
agaggcaaca cttaaacact agggctactg tggcatctat gtagacagga aagacaaacg    60

<210> SEQ ID NO 29
<211> LENGTH: 60
<212> TYPE: DNA
<213> ORGANISM: Artificial
<220> FEATURE:
<223> OTHER INFORMATION: probe

<400> SEQUENCE: 29
gaaaataaac tggaatgatc atctatggct tgggccgctt aggaacaaga accggagaga    60

<210> SEQ ID NO 30
<211> LENGTH: 60
<212> TYPE: DNA
<213> ORGANISM: Artificial
<220> FEATURE:
<223> OTHER INFORMATION: probe

<400> SEQUENCE: 30
agagctacag gaaatggttg tttctcctat actttgtcct taacatcttt cttgatccta    60

<210> SEQ ID NO 31
<211> LENGTH: 60
<212> TYPE: DNA
<213> ORGANISM: Artificial
<220> FEATURE:
<223> OTHER INFORMATION: probe

<400> SEQUENCE: 31
ctgtctccct gtttgtgtaa acatactaga gtatactgcg gcgtgttttc tgtctaccca    60

<210> SEQ ID NO 32
<211> LENGTH: 60
<212> TYPE: DNA
<213> ORGANISM: Artificial
<220> FEATURE:
<223> OTHER INFORMATION: probe

<400> SEQUENCE: 32
tcatccttcc aaaggggcca gttgttctgt gcacttgtcc accctgtta cccccaggat     60

<210> SEQ ID NO 33
<211> LENGTH: 60
<212> TYPE: DNA
<213> ORGANISM: Artificial
<220> FEATURE:
<223> OTHER INFORMATION: probe

<400> SEQUENCE: 33
caaacacaga actggaaaag cagatggtct gactgtgcta tggcctcatc atcaagactt    60

<210> SEQ ID NO 34
<211> LENGTH: 60
<212> TYPE: DNA
<213> ORGANISM: Artificial
<220> FEATURE:
<223> OTHER INFORMATION: probe

<400> SEQUENCE: 34
```

```
tggtggcagg gccatgggag gttggaaggc acccacatcc ttaaagccat cagtagctat      60

<210> SEQ ID NO 35
<211> LENGTH: 60
<212> TYPE: DNA
<213> ORGANISM: Artificial
<220> FEATURE:
<223> OTHER INFORMATION: probe

<400> SEQUENCE: 35
ctgtctctgc tgcagacttg gagaagtatg aaaaatggat ggttgaatttt ggatctgctt     60

<210> SEQ ID NO 36
<211> LENGTH: 60
<212> TYPE: DNA
<213> ORGANISM: Artificial
<220> FEATURE:
<223> OTHER INFORMATION: probe

<400> SEQUENCE: 36
tcctagaaaa cccattgtgt ctctggatct ctagcacatt actaaaagag cctctgcttt      60

<210> SEQ ID NO 37
<211> LENGTH: 60
<212> TYPE: DNA
<213> ORGANISM: Artificial
<220> FEATURE:
<223> OTHER INFORMATION: probe

<400> SEQUENCE: 37
gaattgtcca gagaatcaag gattttttgc ggaatcttgt acccaggaca gagtcctagt     60

<210> SEQ ID NO 38
<211> LENGTH: 60
<212> TYPE: DNA
<213> ORGANISM: Artificial
<220> FEATURE:
<223> OTHER INFORMATION: probe

<400> SEQUENCE: 38
gagaacgtcg ctatggaacc tgcatctacc agggaagact ctgggcattc tgctgctgag      60

<210> SEQ ID NO 39
<211> LENGTH: 60
<212> TYPE: DNA
<213> ORGANISM: Artificial
<220> FEATURE:
<223> OTHER INFORMATION: probe

<400> SEQUENCE: 39
ccaaaagtgt tgttggcaa ttattcccct aggctgagcc tgctcatgta cctctgatta      60

<210> SEQ ID NO 40
<211> LENGTH: 60
<212> TYPE: DNA
<213> ORGANISM: Artificial
<220> FEATURE:
<223> OTHER INFORMATION: probe

<400> SEQUENCE: 40
atatttggga ccacagtatg tcgcaggcat tactaatctg aaaaagtgct caacctcccc      60

<210> SEQ ID NO 41
<211> LENGTH: 60
<212> TYPE: DNA
<213> ORGANISM: Artificial
```

```
<220> FEATURE:
<223> OTHER INFORMATION: probe

<400> SEQUENCE: 41
gggccatatg cacaaatatt gtaactcttg gtatctttac tgcatcatag tcaataaact    60

<210> SEQ ID NO 42
<211> LENGTH: 60
<212> TYPE: DNA
<213> ORGANISM: Artificial
<220> FEATURE:
<223> OTHER INFORMATION: probe

<400> SEQUENCE: 42
ttgtttttat gttcatttgc tggagcgcaa gacgtgctga cacagtgagt tttctctgat    60
```